(12) United States Patent
Ito et al.

(10) Patent No.: US 9,516,993 B2
(45) Date of Patent: Dec. 13, 2016

(54) ENDOSCOPE SYSTEM

(71) Applicant: OLYMPUS CORPORATION, Tokyo (JP)

(72) Inventors: Mitsuhiro Ito, Akiruno (JP); Syunya Akimoto, Kawasaki (JP); Junichi Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/736,710

(22) Filed: Jun. 11, 2015

(65) Prior Publication Data
US 2015/0272423 A1 Oct. 1, 2015

Related U.S. Application Data

(63) Continuation of application No. PCT/JP2014/053876, filed on Feb. 19, 2014.

(30) Foreign Application Priority Data

Mar. 27, 2013 (JP) .................. 2013-067408

(51) Int. Cl.
A61B 1/00 (2006.01)
A61B 6/12 (2006.01)
(Continued)

(52) U.S. Cl.
CPC ......... *A61B 1/00009* (2013.01); *A61B 1/0005* (2013.01); *A61B 1/00055* (2013.01);
(Continued)

(58) Field of Classification Search
CPC . A61B 1/00009; A61B 5/0084; A61B 5/1076; A61B 5/1079; A61B 1/04; A61B 1/0002; A61B 1/00055; A61B 5/7246; A61B 1/0005; A61B 1/2676; A61B 5/7282
See application file for complete search history.

(56) References Cited

U.S. PATENT DOCUMENTS 8,465,452 B2 * 6/2013 Kassab .................. A61B 5/053
604/95.01
2004/0059263 A1 * 3/2004 DeVore ................ A61B 5/1076
600/587
(Continued)

FOREIGN PATENT DOCUMENTS

EP 2554103 A1 2/2013
JP 2005-338551 A 12/2005
(Continued)

OTHER PUBLICATIONS

International Search Report dated Apr. 28, 2014 issued in PCT/JP2014/053876.
(Continued)

*Primary Examiner* — Bo J Peng
(74) *Attorney, Agent, or Firm* — Scully, Scott, Murphy & Presser, P.C.

(57) ABSTRACT

An endoscope system includes an endoscope including an image pickup section that picks up an image of a subject lumen organ, a recording section that records three-dimensional image information of a lumen organ acquired from a medical diagnosis apparatus, a position estimating section that estimates a distal end position of the endoscope, a lumen-diameter acquiring section that acquires a lumen diameter of the organ in the estimated position of the distal end, a condition determining section that determines whether the acquired lumen diameter is smaller than the reference lumen diameter, an image-change-amount detecting section that detects a change amount of a predetermined parameter in an endoscopic image picked up by the image pickup section, a virtual-endoscopic-image generating sec-
(Continued)

tion that generates a virtual endoscopic image from any visual point position, and an information recording section that records a position of a distal end of an insertion section and the virtual endoscopic image.

13 Claims, 20 Drawing Sheets

(51) Int. Cl.
  *A61B 1/04*   (2006.01)
  *A61B 1/267*   (2006.01)
  *A61B 5/00*   (2006.01)
  *A61B 5/107*   (2006.01)
  *A61B 6/00*   (2006.01)
  *G06T 19/00*   (2011.01)
  *A61B 6/03*   (2006.01)
  *A61B 5/06*   (2006.01)

(52) U.S. Cl.
  CPC ............ *A61B 1/00193* (2013.01); *A61B 1/04* (2013.01); *A61B 1/2676* (2013.01); *A61B 5/0084* (2013.01); *A61B 5/066* (2013.01); *A61B 5/1076* (2013.01); *A61B 5/1079* (2013.01); *A61B 5/7246* (2013.01); *A61B 5/7282* (2013.01); *A61B 6/032* (2013.01); *A61B 6/12* (2013.01); *A61B 6/5223* (2013.01); *A61B 6/5247* (2013.01); *G06T 19/003* (2013.01); *A61B 1/0002* (2013.01); *A61B 5/065* (2013.01); *A61B 2034/2065* (2016.02); *G06T 2207/10068* (2013.01); *G06T 2210/41* (2013.01)

(56) References Cited

U.S. PATENT DOCUMENTS

| | | |
|---|---|---|
| 2004/0116775 A1 | 6/2004 | Taniguchi et al. |
| 2009/0292175 A1 | 11/2009 | Akimoto et al. |
| 2011/0184238 A1 | 7/2011 | Higgins et al. |
| 2011/0282151 A1 | 11/2011 | Trovato et al. |
| 2012/0302878 A1 | 11/2012 | Liu et al. |
| 2013/0023730 A1 | 1/2013 | Kitamura et al. |

FOREIGN PATENT DOCUMENTS

| | | |
|---|---|---|
| JP | 2009-279250 A | 12/2009 |
| JP | 2011-212244 A | 10/2011 |
| JP | 2012-505695 A | 3/2012 |
| JP | 2013-517909 A | 5/2013 |
| JP | 2013-519486 A | 5/2013 |
| WO | 2007/100846 A2 | 9/2007 |
| WO | WO 2007/129493 A1 | 11/2007 |
| WO | WO 2011/094518 A2 | 8/2011 |
| WO | WO 2011/101754 A1 | 8/2011 |
| WO | 2012/095755 A1 | 7/2012 |

OTHER PUBLICATIONS

Japanese Office Action dated Dec. 2, 2014 issued in JP 2014-549267.
Extended Supplementary European Search Report dated Jul. 5, 2016 in related European Application No. 14 77 6199.3.

* cited by examiner

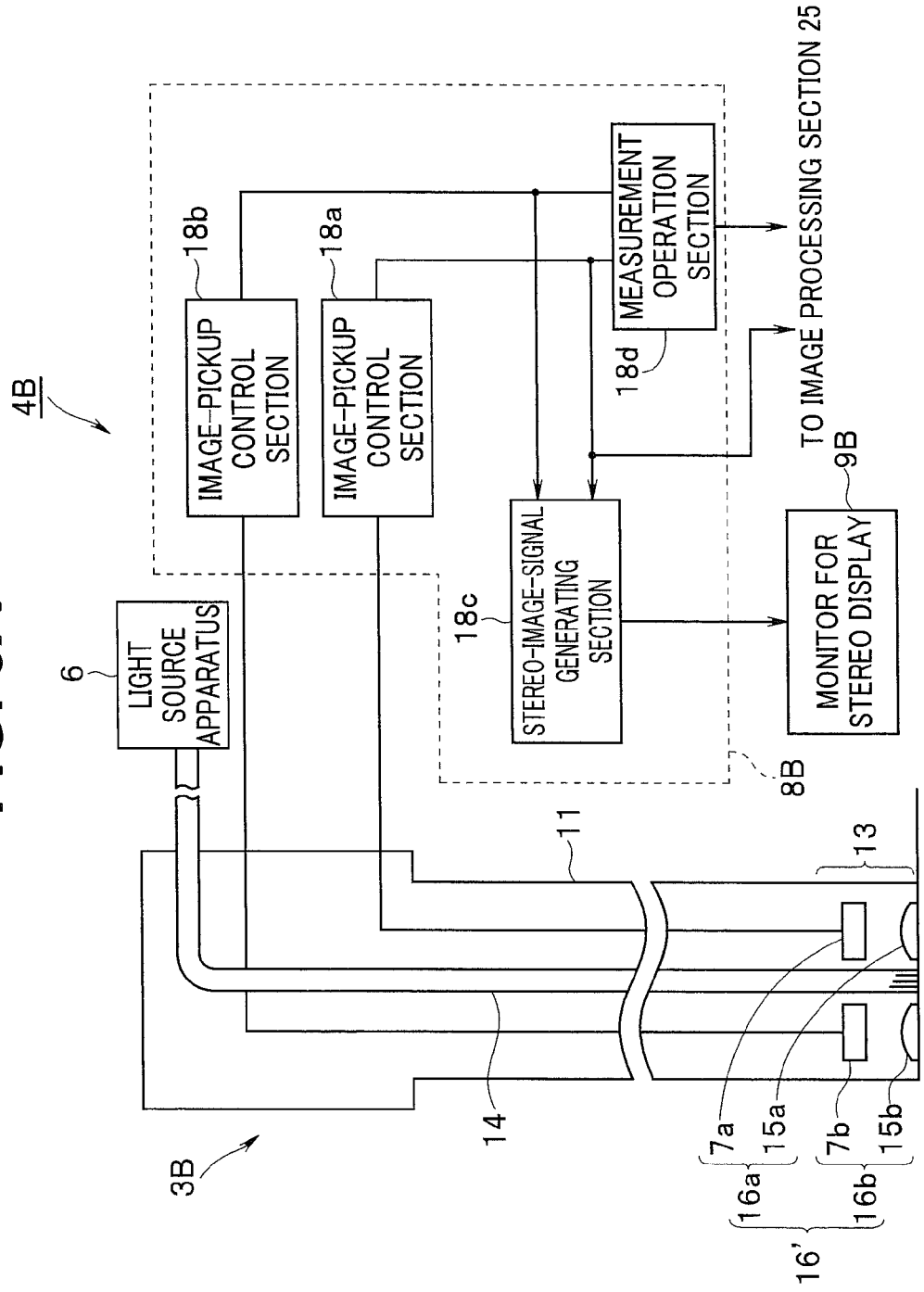

ENDOSCOPE SYSTEM

CROSS REFERENCE TO RELATED APPLICATION

This application is a continuation application of PCT/JP2014/053876 filed on Feb. 19, 2014 and claims benefit of Japanese Application No. 2013-067408 filed in Japan on Mar. 27, 2013, the entire contents of which are incorporated herein by this reference.

BACKGROUND OF THE INVENTION

1. Field of the Invention

The present invention relates to an endoscope system that picks up an image of an inside of a subject with image pickup means.

2. Description of the Related Art

In recent years, an endoscope including an insertion section insertable into a body cavity and the like has been widely used in a medical field and the like.

On the other hand, when the endoscope is inserted into a lumen organ complexly branching like a bronchus in the body cavity to examine (a diseased tissue of) a target region of the periphery side of the lumen organ or perform a biopsy or treatment by a treatment instrument, it is sometimes difficult to introduce an insertion section distal end near the target region using only an endoscopic image obtained when the endoscope is inserted.

Therefore, a system and an apparatus for supporting operation for introducing the insertion section distal end of the endoscope near the target region have been proposed.

For example, a medical image observation supporting apparatus of International Publication No. 2007-129493 cited as a first conventional example discloses a configuration including a CT-image-data capturing section, a CT-image-data storing section, an information extracting section, an anatomical information database, a visual-point-position/visual-line-direction setting section, a lumen-organ-image generating section, an anatomical-name-information generating section, a branch designating section, an image combining and displaying section, and a user-I/F control section. The visual-point-position/visual-line-direction setting section locks on, on the basis of structure information of a lumen organ extracted by the information extracting section, a visual point in a substantially center axis of the lumen organ and sets a visual point position and a visual line direction for observing an external appearance of the lumen organ.

A medical apparatus of Japanese Patent Application Laid-Open Publication No. 2009-279250 cited as a second conventional example includes virtual-endoscopic-image generating means for generating, from three-dimensional image data of a bronchus acquired in advance, virtual endoscopic images from a plurality of different visual line positions, image retrieving means for retrieving a virtual endoscopic image having high similarity to a real image, reference-point setting means for setting a reference point on the basis of a position of a visual line of the virtual endoscopic image having the high similarity, relative-position calculating means for calculating a relative position of a treatment instrument with respect to the reference point, movement detecting means for detecting movement of the reference point or the bronchus, and position correcting means for correcting the relative position according to the movement of the reference point or the bronchus.

When a position of an insertion section distal end of an endoscope is estimated, the estimation is performed by comparison of an endoscopic image (a real image) picked up by image pickup means of the endoscope and a virtual endoscopic image (a virtual image) generated on the basis of three-dimensional data of a lumen organ by CT. Therefore, first, alignment by the comparison of both the images is performed.

When accuracy of the estimation of the position is deteriorated, re-alignment for setting the endoscope in a state in which predetermined accuracy can be secured is necessary.

The first conventional example discloses a viewpoint of coordinate-converting an endoscope distal end position into a three-dimensional image and comparing a distance between the endoscope distal end position and a core line and a viewpoint of comparing a real image (an endoscopic image) and a virtual image (a virtual endoscopic image) of a branch section and also discloses recording of feature information and the like of the branch section.

SUMMARY OF THE INVENTION

An endoscope system according to an aspect of the present invention includes: an endoscope including an image pickup section configured to pick up an image of a lumen organ of a subject; a recording section configured to record three-dimensional image information of a lumen organ of the subject acquired from a medical diagnosis apparatus different from the endoscope; a position estimating section configured to estimate a position of a distal end of an insertion section of the endoscope; a lumen-diameter acquiring section configured to acquire, on the basis of the three-dimensional image information recorded by the recording section, a lumen diameter of the lumen organ of the subject at the position of the distal end of the insertion section of the endoscope estimated by the position estimating section; a condition determining section configured to determine, on the basis of the lumen diameter acquired by the lumen-diameter acquiring section and a reference lumen diameter set in advance, whether the lumen diameter acquired by the lumen-diameter acquiring section is smaller than the reference lumen diameter; an image-change-amount detecting section configured to detect, when the condition determining section determines that the lumen diameter acquired by the lumen-diameter acquiring section is smaller than the reference lumen diameter, a change amount of a predetermined parameter concerning an endoscopic image picked up by the image pickup section involved in an inserting action of the insertion section of the endoscope; a virtual-endoscopic-image generating section configured to generate, on the basis of the three-dimensional image information recorded by the recording section, a virtual endoscopic image endoscopically rendered from any visual point position; and an information recording section configured to record, when the change amount of the predetermined parameter concerning the endoscopic image detected by the image-change-amount detecting section is larger than a reference set value set in advance, the position of the distal end of the insertion section of the endoscope and the virtual endoscopic image corresponding to the position of the distal end of the insertion section of the endoscope.

BRIEF DESCRIPTION OF THE DRAWINGS

FIG. 3A is a diagram showing a configuration of an endoscope apparatus including a stereo endoscope that performs stereo measurement;

DETAILED DESCRIPTION OF THE PREFERRED EMBODIMENT

Embodiments of the present invention are explained below with reference to the drawings.

First Embodiment

Figure 1:
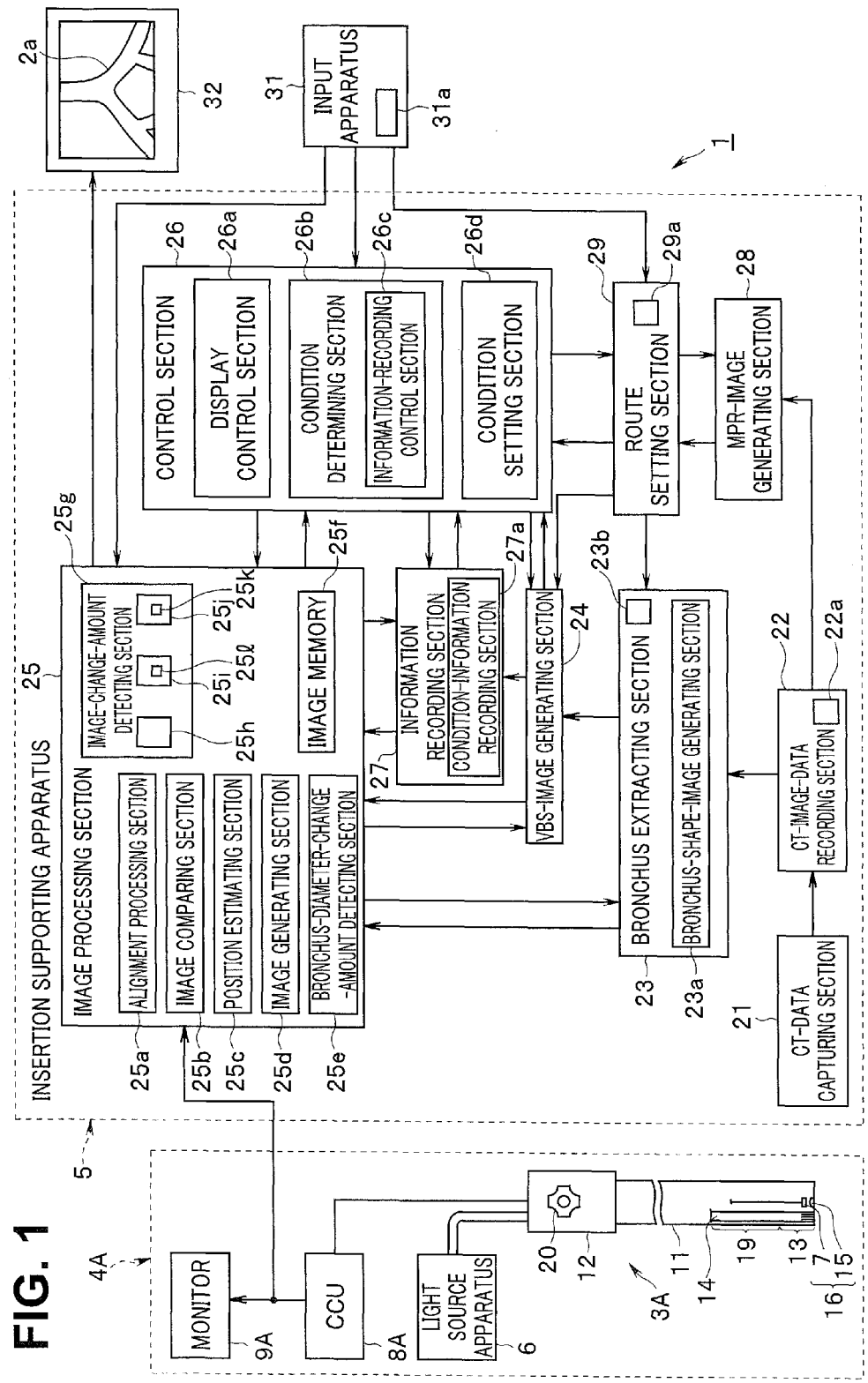
FIG. 1 is a diagram showing an overall configuration of an endoscope system in a first embodiment of the present invention.

As shown in FIG. 1, an endoscope system 1 in a first embodiment of the present invention is mainly configured from an endoscope apparatus 4A including an endoscope 3A inserted into a bronchus 2 (FIG. 2A) set as a predetermined lumen organ in a patient treated as a subject, which is a test target, and an insertion supporting apparatus 5 used together with the endoscope apparatus 4A to perform insertion support of the endoscope 3A.

The endoscope apparatus 4A includes the endoscope 3A, a light source apparatus 6 that supplies illumination light to the endoscope 3A, a camera control unit (abbreviated as CCU) 8A functioning as a signal processing apparatus that performs signal processing for an image pickup device 7, which configures image pickup means mounted on the endoscope 3A, and a monitor 9A that displays an endoscopic image generated by the CCU 8A.

The endoscope 3A includes an elongated insertion section (or an endoscope insertion section) 11 having flexibility and an operation section 12 provided at a rear end of the insertion section 11. An illumination window and an observation window are provided at a distal end portion 13 of the insertion section 11. A light guide 14 that transmits the illumination light is inserted through the operation section 12. An incident end of the light guide 14 is connected to the light source apparatus 6. The illumination light generated by a not-shown light source lamp or a not-shown LED in the light source apparatus 6 is made incident on the incident end. The illumination light transmitted by the light guide 14 is emitted forward from an emission end (a distal end face) attached to the illumination window.

An objective lens 15 forming an objective optical system that forms an image of the subject is attached to the observation window. The image pickup device 7 such as a CCD is disposed in an image forming position of the objective lens 15. An image pickup apparatus 16 functioning as image pickup means for picking up an image of an inside of the bronchus 2 set as the predetermined lumen organ, into which the insertion section 11 is inserted, is formed by the objective lens 15 and the image pickup device 7.

The image pickup device 7 is connected to the CCU 8A via a signal line inserted through the insertion section 11 and the operation section 12. The CCU 8A generates, with a not-shown image signal generation circuit on an inside of the CCU 8A, an image signal of a picked-up image corresponding to an optical image formed on an image pickup surface of the image pickup device 7 and outputs the image signal to the monitor 9A. The monitor 9A displays an image (a movie) of the image signal as an endoscopic image (also referred to as picked-up image).

In the insertion section 11 of the endoscope 3A, a bendable bending section 19 is provided at a rear end of the distal end portion 13. A surgeon can bend the bending section 19 in any up-down and left-right directions by performing operation for, for example, rotating a bending operation knob 20 provided in the operation section 12. Note that the bending operation knob 20 includes a bending operation knob for up and down direction for bending the bending section 19 in the up-down direction and a bending operation knob for left-right direction for bending the bending section 19 in the left-right direction.

An endoscope apparatus 4B shown in FIG. 3A may be adopted instead of the endoscope apparatus 4A shown in FIG. 1.

The endoscope apparatus 4B includes a stereo endoscope 3B capable of performing stereoscopic measurement (stereo measurement), the light source apparatus 6, a CCU 8B that performs signal processing for two image pickup devices 7a and 7b provided in the stereo endoscope 3B, and a monitor for stereo display 9B that displays a stereo image signal generated by the CCU 8B.

In the distal end portion 13 of the insertion section 11 of the stereo endoscope 3B, left and right objective lenses 15a and 15b are disposed in a predetermined space apart from each other in the left-right direction. The left and right image pickup devices 7a and 7b are disposed in image forming positions of the objective lenses 15a and 15b. A stereo image pickup apparatus 16' including left and right image pickup apparatuses 16a and 16b is configured. Note that, as the left and right objective lenses 15a and 15b and the left and right image pickup apparatuses 16a and 16b, objective lenses and the image pickup apparatuses respectively having same characteristics are used.

The light guide 14 that transmits illumination light from the light source apparatus 6 is inserted through the insertion section 11. A distal end of the light guide 14 is attached to the illumination window of the distal end portion 13. The light guide 14 emits the transmitted illumination light from the illumination window and illuminates an object such as a diseased part in a body cavity.

The left and right image pickup devices 7a and 7b, which pick up images of the illuminated object, input photoelectrically-converted image pickup signal to image-pickup control sections 18a and 18b in the CCU 8. The image-pickup control sections 18a and 18b generate left and right image signals and output the left and right image signals to a stereo-image-signal generating section 18c.

The stereo-image-signal generating section 18c generates an image signal for stereo display from the left and right image signals and outputs the image signal for stereo display to a monitor for stereo display 9B. The monitor for stereo display 9B displays the image signal for stereo display. A user such as the surgeon is capable of stereoscopically viewing the object through the display of the image signal for stereo display.

The left and right image signals generated by the image-pickup control sections 18a and 18b are inputted to a measurement operation section 18d. The measurement operation section 18d makes it possible to measure, for example, a distance between two points on a picked-up image through stereo measurement, which makes use of a principle of triangulation, using the left and right image signals. As explained below, it is possible to measure, for example, a bronchus diameter Den. Note that information such as the bronchus diameter Den calculated by the measurement operation section 18d is outputted to an image processing section 25. A video signal generated by the image-pickup control section 18a (or 18b) is also outputted to the image processing section 25.

Next, a method of calculating a three-dimensional coordinate of a point (a position) of a measurement target by the stereo measurement is explained with reference to FIG. 3B. A three-dimensional coordinate (X, Y, Z) of a measurement point 60 is calculated by Equation (1) to Equation (3) below by a method of triangulation with respect to images of image pickup surfaces of the image pickup devices 7a and 7b using the left and right objective lenses 15a and 15b. In the equations, two-dimensional coordinates of measurement points 61 and 62 on left and right images applied with distortion correction are respectively represented as $(X_L, Y_L)$ and $(X_R, Y_R)$, a distance between optical centers 63 and 64 of the left and right objective lenses 15a and 15b is represented as D, a focal length is represented as F, and $t=D/(X_L-X_R)$. Then, a following relational expression holds.

$$X = t \times X_R + D/2 \tag{1}$$

$$Y = t \times Y_R \tag{2}$$

$$Z = t \times F \tag{3}$$

When the measurement points 61 and 62 of the two-dimensional coordinates on the images with respect to the measurement point 60 are determined as explained above, a three-dimensional coordinate of the measurement point 60 is calculated using a distance D and a focal length F serving as parameters.

By calculating three-dimensional coordinates of several points, it is possible to perform various kinds of measurement of distances between two points, distances between a line connecting the two points and one point, areas, depths, surface shapes, and the like are possible. It is also possible to calculate a distance from the optical center 63 of the left objective lens 15a or the optical center 64 of the right objective lens 15b to the object (an object distance). In order to perform the stereo measurement, optical data indicating characteristics of the distal end portion 13 and the objective lens 15a and 15b of the endoscope 3B is used. Note that, in FIG. 3B, a surface including both of the two image pickup surfaces is indicated by PL. A center of the right image pickup surface (which is on optical axes of the objective lenses 15a and 15b not shown in FIG. 3B) is indicated by $O_L$ and $O_R$.

As a method of calculating the three-dimensional coordinate from the stereo image, for example, there is a method disclosed in Japanese Patent Application Laid-Open Publication 2011-027911.

In the present embodiment, when the bronchus diameter Den is measured from an endoscopic image explained below, the bronchus diameter Den is calculated by designating the measurement points 61 and 62 on an image corresponding to one measurement point 60 of the bronchus diameter on the imaging surface shown in FIG. 3B and a point corresponding to the other measurement point.

This method is explained with reference to FIG. 3C and FIG. 3D. A state in which a bronchus 72 in an endoscopic image and a next bronchus branch section 73, which is a periphery side of the bronchus 72, are displayed on a display screen 71 of the monitor 9B is shown. A range of this screen 71 is divided by blocks indicated by a mesh 74. Areas where average luminance is a predetermined value or less in the respective blocks are extracted. A detection block 75 extracted in this way is shown with hatching in FIG. 3D.

A place where a diameter is the largest in the detection block 75 is set as a measurement target bronchus diameter to set a measurement point 60a and a measurement point 60b. In general, when a lumen organ is observed by an endoscope, an image is darker in a deeper place. Therefore, it is possible to set the measurement points by the method explained above. When the measurement points 60a and 60b are designated, the measurement points 60a and 60b may be designated in a direction in which a space between the measurement points 60a and 60b is the largest.

The calculation explained above is carried out on both of the left screen and the right screen configuring the stereo image to calculate points respectively corresponding to the measurement point 60a and the measurement point 60b on both the left screen and the right screen. Then, when the point equivalent to the measurement point 60a on the left screen is calculated as the measurement point 61 shown in FIG. 3B and a point equivalent to the measurement point 60a on the right screen is calculated as the measurement point 62, the position of the measurement point 60 can be calculated. By performing the same calculation for the left screen and the right screen equivalent to the measurement point 60b, a three-dimensional coordinate equivalent to the measurement points 60 at both ends of the bronchus diameter can be obtained. Therefore, it is possible to calculate the bronchus diameter Den from a distance between these two points.

By performing the operation explained above every time the endoscopic image is updated, it is possible to monitor a change in the bronchus diameter Den from the endoscopic image.

The stereo measurement may be performed as explained below using the endoscope 3A including a monocular (single) image pickup apparatus 16 shown in FIG. 1 instead of using the stereo endoscope 3B including the stereo image pickup apparatus 16' including the pair of left and right image pickup apparatuses 16a and 16b shown in FIG. 3A.

Figure 3B:
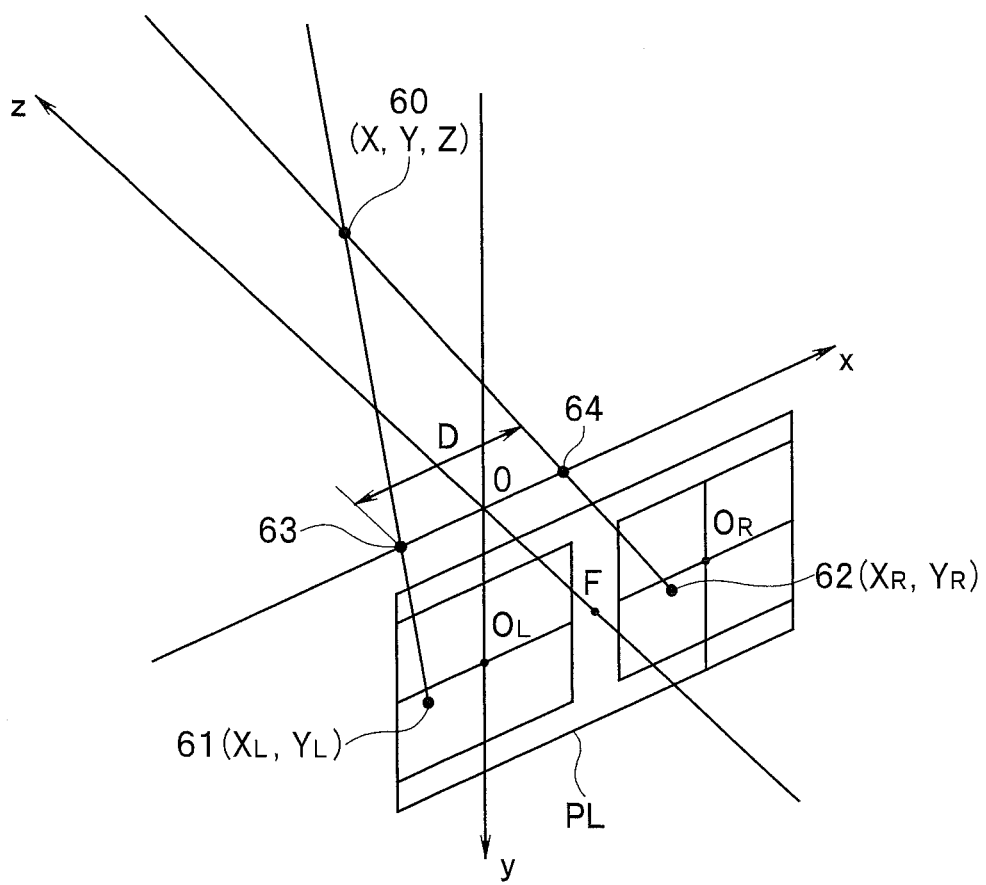
FIG. 3B is an explanatory diagram showing a relation in which an image of a position of a measurement target, for which the stereo measurement is performed, is formed on image pickup surfaces of left and right image pickup devices.
Figure 3C:
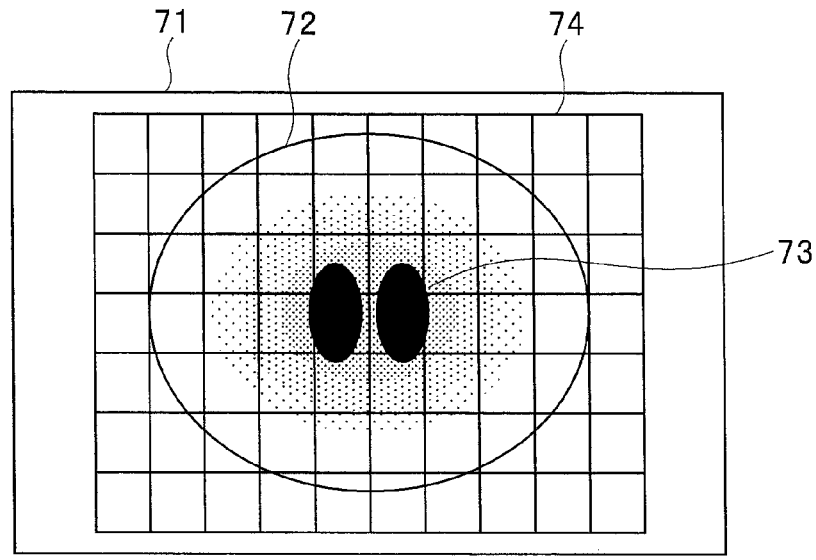
FIG. 3C is a diagram showing an example in which an image obtained by picking up an image in the bronchus using the stereo endoscope is displayed on a monitor screen.
Figure 3D:
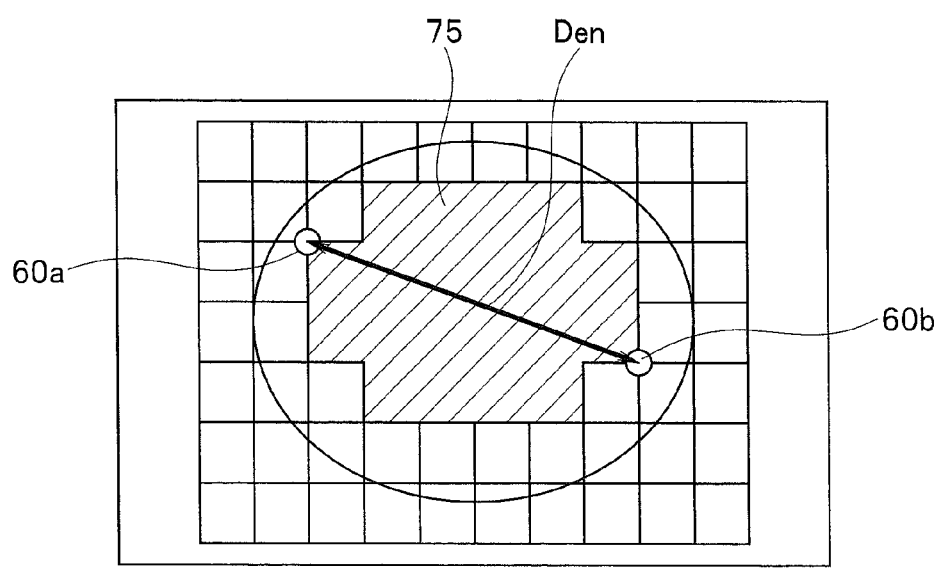
FIG. 3D is an explanatory diagram for calculating the bronchus diameter from the image shown in FIG. 3C.
Figure 3E:
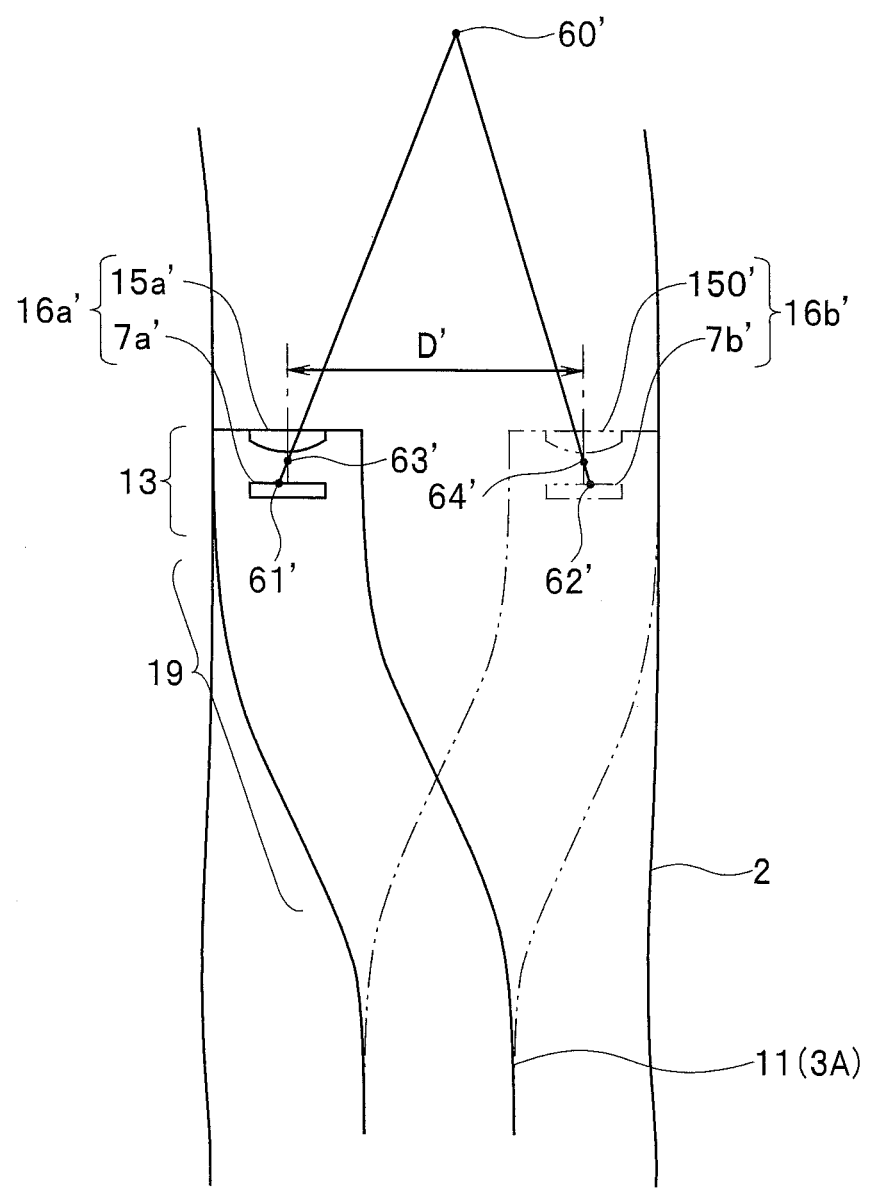
FIG. 3E is an explanatory diagram for calculating the bronchus diameter with the stereo measurement using a single image pickup apparatus.

When the endoscope 3A is inserted into the bronchus 2 as shown in FIG. 3E, the surgeon may bend the bending section 19 on the distal end side of the insertion section 11 to the left and right and set the endoscope 3A in a state substantially equivalent to a state in which image pickup is performed with the left and right image pickup apparatuses shown in FIG. 3B and calculate the bronchus diameter through the stereo measurement.

For example, in a state in which the bending section 19 is not bent, the distal end of the insertion section 11 is set near a center line of the bronchus 2. The surgeon bends the bending section 19 to, for example, the left side, brings the distal end of the insertion section 11 into contact with an inner wall on a left side of the bronchus 2, and sets the endoscope 3A in a first image pickup position 16a' equivalent to a state in which image pickup is performed with the left image pickup apparatus 16a shown in FIG. 3B. The objective lens 15 and the image pickup device 7 in the first image pickup position 16a' are respectively indicated by 15a' and 7a'.

After the image pickup is performed in the first image pickup position 16a', the surgeon bends the bending section 19 to a right side, brings the distal end into contact with an inner wall on a right side of the bronchus 2 as indicated by an alternate long and two dashes line in FIG. 3E, and sets the endoscope 3A in a second image pickup position 16b' equivalent to a state in which image pickup is performed with the right image pickup apparatus 16b shown in FIG. 3B. The objective lens 15 and the image pickup device 7 in the second image pickup position 16b' are respectively indicated by 15b' and 7b'. The image pickup is performed in the second image pickup position 16b'.

Information such as movement amounts to the left and right of the distal end portion 13 in the case in which the bending section 19 is bent to the left and right by operation of the bending operation knob 20, a focal length of the objective lens 15 of the image pickup apparatus 16, the numbers of pixels in left-right and vertical directions of the image pickup device 7, and a pitch of pixels is checked in advance and stored in an information recording section 27 or the like.

In such a case, optical centers 63' and 64' in FIG. 3E corresponding to the left and right optical centers 63 and 64 shown in FIG. 3B and a distance D' corresponding to the distance D between the left and right optical centers can be calculated from, for example, a bending angle of the bending section 19 (an operation amount of the bending operation knob 20). A three-dimensional position of the measurement point 60' can be calculated from information concerning the measurement points 61' and 62' on the image pickup devices 7a' and 7b' for the measurement point 60' corresponding to the case of the measurement point 60 shown in FIG. 3B. By designating two points of one position and the other position of the bronchus diameter as the measurement point 60', it is possible to calculate the bronchus diameter. In this way, the bronchus diameter may be calculated using the endoscope 3A shown in FIG. 1. Note that, in the above explanation, the bending section 19 is bent to the left and right directions. However, when the bending section 19 is bent to another direction as well, it is possible to calculate a bronchus diameter along the other direction.

As shown in FIG. 1, the insertion supporting apparatus 5 includes a CT-data capturing section 21 that captures, for a patient who undergoes a test by the endoscope 3A or 3B, via a portable storage medium such as a DVD, a blu-ray disk, or a flash memory, CT data serving as three-dimensional image information of the patient generated by publicly-known CT (computed tomography) and a CT-image-data recording section 22 functioning as image recording means for recording the CT data captured by the CT-data capturing section 21.

Note that the CT-image-data recording section 22 may store, through a communication line, the Internet, or the like, the CT data (serving as the three-dimensional image information of the patient treated as the subject) generated by the CT. The CT-image-data recording section 22 can be configured by a hard disk apparatus, a flash memory, a DVD, or the like.

The CT-image-data recording section 22 configuring the image recording means includes an association-image-information recording section 22a that records association image information in which CD image data separated from the CT data and three-dimensional position data obtained using a first coordinate system (a CT coordinate system) corresponding to CT image data obtained by separating position information from the CT data are associated with each other.

The insertion supporting apparatus 5 includes a bronchus extracting section 23 including a lumen organ extraction circuit functioning as lumen organ extracting means for extracting three-dimensional image data of the bronchus 2 set as the predetermined lumen organ from the CT image data of the CT-image-data recording section 22.

The bronchus extracting section 23 generates three-dimensional shape information (shape data) and three-dimensional shape image information (image data) from extracted three-dimensional data (more specifically, three-dimensional volume data) of the bronchus 2. That is, the bronchus extracting section 23 includes a bronchus-shape-image generating section 23a functioning as bronchus-shape-image generating means for generating a bronchus shape image 2a serving as an image of a bronchus shape of a hollow three-dimensional shape from the extracted three-dimensional data of the bronchus 2.

When extracting the three-dimensional data of the bronchus 2, the bronchus extracting section 23 extracts the three-dimensional data in association with three-dimensional position data in the first coordinate system (or the CT coordinate system) corresponding to the three-dimensional data. The bronchus extracting section 23 includes an association-information recording section 23b including a memory that records association information in which three-dimensional shape data (i.e., bronchus shape data) and three-dimensional position data of the bronchus 2 are associated with each other. The association-image-information recording section 23b records, in a lookup table or the like, data of a bronchus diameter in a designated (three-dimensional) position. It is possible to read out the data of the bronchus diameter corresponding to the designated position from the association-information recording section 23b and acquire data of the bronchus diameter. Note that the bronchus diameter may be acquired from the bronchus shape data without using the association-information recording section 23b.

The insertion supporting apparatus 5 includes a VBS-image generating section 24 functioning as virtual-endoscopic-image generating means for generating a virtual endoscopic image (referred to as VBS image) serving as a virtual endoscopic image corresponding to the endoscopic image generated by the image pickup of the image pickup apparatus 16 or 16a and 16b provided at the distal end portion 13 of the insertion section 11 in the endoscope 3A or 3B. In the following explanation, when either the endoscope 3A or the endoscope 3B may be used, the endoscope 3A is referred to.

Characteristic information including an image forming system concerning the image pickup apparatus 16 of the distal end portion 13 of the endoscope 3A (a focal length of the objective lens 15, the number of pixels of the image pickup device 7, a pixel size, and the like) is inputted to the VBS-image generating section 24 from, for example, an input apparatus 31 through a control section 26. The characteristic information concerning the image pickup apparatus 16 may be inputted from the input apparatus 31 to the VBS-image generating section 24 not through the control section 26.

The VBS-image generating section 24 generates, on the basis of information concerning a three-dimensional position of the image pickup apparatus 16 disposed in the distal end portion 13 of the endoscope 3A actually inserted into the bronchus 2 (which can be considered a three-dimensional position of the distal end of the insertion section 11), characteristic information for forming an image of an object in the bronchus 2 by the image pickup apparatus 16, and bronchus shape data, a VBS image that virtually renders an endoscopic image obtained by endoscopically picking up the inside of the bronchus 2 with the three-dimensional position (also simply referred to as position) set as a visual point position. Note that when an axial direction of the distal end (substantially coinciding with an optical axial direction of the image pickup apparatus 16) is changed in the same visual point position, the VBS-image generating section 24 can generate a VBS image corresponding to the change.

Therefore, for example, when a position of the distal end of the insertion section 11 and a (axis) direction of the distal end are designated by the CT coordinate system, the VBS-image generating section 24 generates a VBS image corresponding to the designation of the position and the direction.

The insertion supporting apparatus 5 includes an image processing section 25 that performs, through image matching, alignment of an endoscopic image inputted from the CCU 8A and a VBS image of the VBS-image generating section 24, the control section 26 functioning as control means for performing control of the image processing section 25 and the like, and the information recording section 27 configuring information recording means for recording, as candidate information, predetermined information such as a VBS image for supporting insertion under control by the control section 26.

The insertion supporting apparatus 5 includes an MPR-image generating section 28 that generates a CT tomography image (referred to as MPR image) serving as a multiple section reconfigured image on the basis of the CT image data recorded in the CT-image-data recording section 22 and a route setting section 29 that generates a route setting screen serving as a setting screen for an insertion route including the MPR image generated by the MPR-image generating section 28 and setting a route in insertion into a target region side in the bronchus 2 of the endoscope 3A.

Figure 2A:
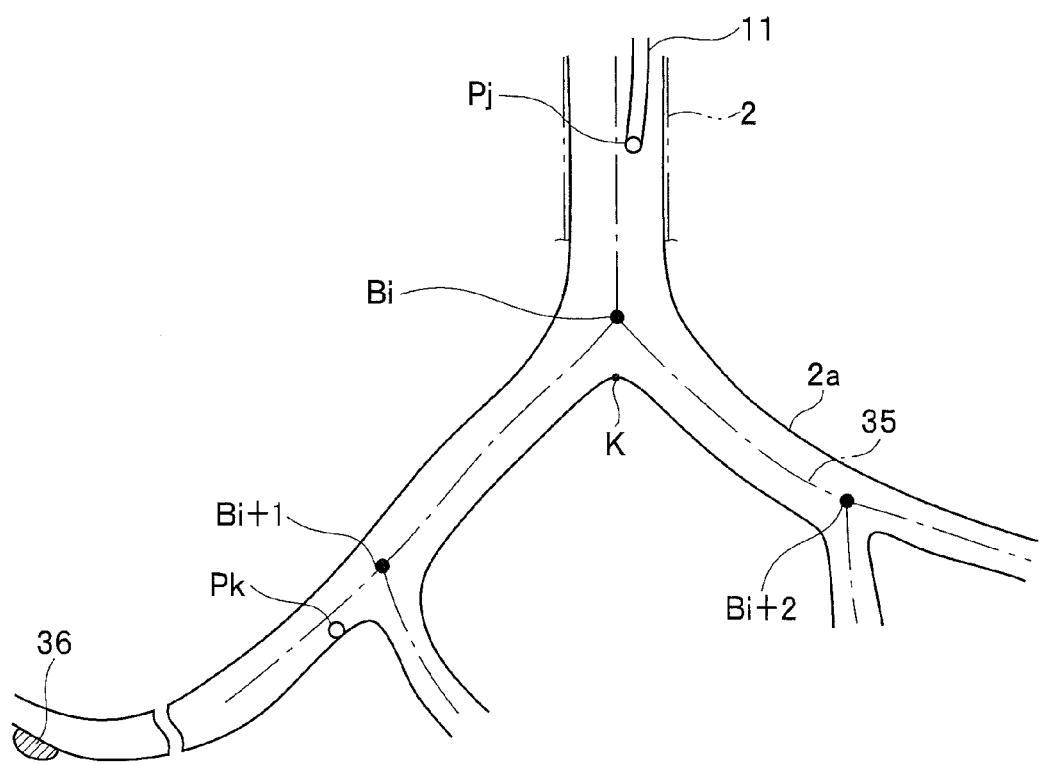
FIG. 2A is a diagram showing a part of a bronchus and a bronchus shape image.

For example, when a target region 36 is designated as shown in FIG. 2A from the CT image data, the route setting section 29 has a function of a route-data generating section 29a that generates, from the CT image data and the bronchus shape image 2a, route data from an insertion start position (of the insertion section 11) in the bronchus 2 to a target position near the target region 36.

The endoscope system 1 includes the input apparatus 31 including a keyboard and a pointing device for inputting setting information to the route setting section 29. The surgeon can input parameters and data in performing image processing from the input apparatus 31 to the image processing section 25 and selects and instructs a control operation to the control section 26.

When the surgeon performs the route setting, the route setting section 29 sends information concerning a set route to the VBS-image generating section 24, the MPR-image generating section 28, and the control section 26. The VBS-image generating section 24 and the MPR-image generating section 28 respectively generate a VBS image and an MPR image along the route. The control section 26 performs control of operations of the respective sections along the route.

An endoscopic image (an actual image or also simply referred to as image) generated by the CCU 8A and the VBS image generated by the VBS-image generating section 24 are inputted to the image processing section 25. The bronchus shape image 2a generated by the bronchus-shape-image generating section 23a is also inputted to the image processing section 25.

In the present embodiment, a sensor that detects the position of the distal end of the insertion section 11 is not mounted on the distal end portion 13 of the insertion section 11 where the image pickup apparatus 16 is disposed. Therefore, a three-dimensional position (a position) of the distal end of the insertion section 11 is estimated (or calculated) by the image matching in an alignment processing section 25a by the image processing section 25.

If a three-dimensional position (a known position) or a position near the three-dimensional position that can be specified by the CT coordinate system such as an entrance of the bronchus 2 or a carina K (see FIG. 2A) is set in advance as a start position of moving image matching, the VBS-image generating section generates a VBS image on the basis of information concerning the position. The alignment processing section 25a of the image processing section 25 sets the distal end of the insertion section 11 in the three-dimensional position (the known position) or the position near the three-dimensional position that can be specified by the CT coordinate system (a first coordinate system) from the bronchus shape image 2a and sets the distal end of the insertion section 11 in a state in which the position of the distal end of the insertion section 11 can be estimated (or calculated) by the CT coordinate system.

The surgeon inserts the distal end of the insertion section 11 such that the endoscopic image can be seen the same as the VBS image. By performing such alignment, the alignment processing section 25a of the image processing section 25 compares the endoscopic image and the VBS image and starts image matching in which, as a result of the comparison, the endoscopic image and the VBS image coincide with each other within a set condition (an error that can secure predetermined accuracy).

Therefore, the image processing section 25 includes an image comparing section 25b functioning as image comparing means for comparing the endoscopic image and the VBS image. The alignment processing section 25a performs processing of alignment by the image matching using the image comparison by the image comparing section 25b.

By performing the alignment explained above, the alignment processing section 25a of the image processing section 25 sets a state in which the position of the distal end of the insertion section 11 and an axial direction of the distal end (a visual point direction or a visual line direction of the image pickup apparatus 16) can be specified (acquired) by information indicating a position coordinate and an axial direction (also referred to as posture) in the CT coordinate system (the first coordinate system).

After the alignment is performed in this way, it is possible to acquire, using information concerning the alignment, the position of the distal end of the insertion section 11 after the alignment as information associated with a position in the CT coordinate system (the first coordinate system) according to an image comparison result by the image comparing section 25b. That is, the image processing section 25 includes, as position-information acquiring means for acquiring the position (information) of the distal end of the insertion section 11, a position estimating section 25c that acquires the position of the distal end of the insertion section 11 by estimating the position. The position estimating section 25c also acquires the position of the distal end of the insertion section 11 on the basis of an image comparison result by the image comparing section 25b. Further, in operation for inserting the insertion section 11 to the depth side (the periphery side) of the bronchus 2, the image processing section 25 estimates, according to the comparison result of both of the endoscopic image and the VBS image, a position to which the distal end of the insertion section 11 moves under the CT coordinate system in a state after the alignment by the alignment processing section 25a.

That is, the image pickup apparatus 16 moves according to the operation for moving (for insertion) the distal end of the insertion section 11 substantially along a core line 35 from the position subjected to the alignment processing. Therefore, the endoscopic image changes.

In this case, the position estimating section 25c selects, using VBS images (outputted from the VBS-image generating section 24) in a case in which the distal end of the insertion section 11 is moved on a route substantially along the core line 35, through image processing, a VBS image best matching a present endoscopic image and calculates (estimates) a three-dimensional position corresponding to the selected VBS image as the position of the distal end of the insertion section 11. As explained above, the position estimating section 25c calculates (estimates) a posture of the distal end of the insertion section 11 together with the position of the distal end of the insertion section 11.

Note that the distal end of the insertion section 11 is sometimes moved in a position deviating from the core line 35. Therefore, the VBS-image generating section 24 may generate a VBS image in a position eccentric from the core line 35 by an appropriate distance and output the generated VBS image to the alignment processing section 25a. Consequently, it is possible to enlarge a range of position estimation by the image matching.

The position estimating section 25c calculates (estimates), from a difference value amount between the two positions estimated by the position estimating section 25c, a movement amount of the distal end of the insertion section 11 and a position to which the distal end of the insertion section 11 moves. The position estimating section 25c can also calculate (estimate) a distance between estimated one position and a specific position like a branch point (a position that can be specified by the CT coordinate system) in a feature region in the bronchus 2.

Therefore, the position estimating section 25c has a function of a distance calculating section functioning as distance calculating means for calculating a distance from the position of the distal end of the insertion section 11 estimated by the position estimating section 25c and a feature region such as a branch region branching in the bronchus 2 set as the predetermined lumen organ. As explained above, the image processing section 25 has a function of the position estimating section 25c functioning as the position-information acquiring means for acquiring information concerning the position of the distal end of the insertion section 11 by estimating the position. In this case, the alignment processing section 25a may be defined as a component including the function of the position estimating section 25c.

Note that, in this specification, the distal end of the insertion section 11 is used in the same meaning as a distal end of the endoscope 3A.

The image processing section 25 generates an image displayed on a monitor 32 functioning as image display means under control by a display control section 26a or the like that controls display in the control section 26.

Under the control by the display control section 26a, usually, the image processing section 25 outputs an image signal (a video signal) of the bronchus shape image 2a generated by the bronchus-shape-image generating section 23a to the monitor 32. On the monitor 32, as shown in FIG. 1, the bronchus shape image 2a is displayed as, for example, a two-dimensional tomography image sliced on a cross section along a direction passing a center of a lumen. Note that the bronchus shape image 2a is not limited to the display as the two-dimensional tomography image and may be displayed as a three-dimensional image. When the bronchus shape image 2a is displayed as the three-dimensional image, for example, the bronchus shape image 2a may be displayed as a projection view by a parallel projection method or may be displayed as a transparent view such that a lumen inside can be seen.

As shown in FIG. 2A, the core line 35 passing the center of the lumen of the bronchus 2 is also displayed in the bronchus shape image 2a displayed on the monitor 32.

Note that, for example, the bronchus-shape-image generating section 23a generates the core line 35. However, the image processing section 25 may generate the core line 35. The image processing section 25 has a function of an image generating section 25d that generates, on the bronchus shape image 2a, together with the core line 35, for example, an image on which the position of the distal end of the insertion section 11 estimated by the position estimating section 25c is superimposed.

When the user such as the surgeon inserts the insertion section 11 into the bronchus 2 with the distal end thereof ahead, the core line 35 and the position of the distal end of the insertion section 11 are displayed on the bronchus shape image 2a representing a three-dimensional shape of the bronchus 2. Therefore, the user can easily perform operation of insertion of the insertion section 11 by referring to the display. By performing operation for inserting the insertion section 11 along the core line 35, the estimation of the position of the distal end of the insertion section 11 by the image matching can be performed in a short time.

The image processing section 25 includes a bronchus-diameter-change-amount detecting section 25e that detects a change amount of the bronchus diameter (in the case of the bronchus 2 set as the predetermined lumen organ) as lumen-diameter-change-amount detecting means for detecting, on the basis of information concerning the position of the distal end of the insertion section 11 estimated by the position estimating section 25c, a change amount of a lumen diameter of the predetermined lumen organ.

The bronchus-diameter-change-amount detecting section 25e has functions of a bronchus-diameter acquiring section functioning as the bronchus-diameter acquiring means for acquiring a bronchus diameter from the CT coordinate system corresponding to a present position of the distal end of the insertion section 11 estimated by the position estimating section 25c and a bronchus-diameter comparing section functioning as bronchus-diameter comparing means for comparing the bronchus diameter acquired by the bronchus-diameter acquiring section and a reference bronchus diameter set in advance. The bronchus-diameter acquiring section sequentially acquires bronchus diameters in respective positions of the distal end of the insertion section 11 estimated during the insertion operation of the insertion section 11 to thereby detect a change amount of the positions of the distal end of the insertion section 11, that is, a change amount of the bronchus diameters.

The bronchus-diameter comparing section compares sequentially-acquired present bronchus diameters and the reference bronchus diameter. In the present embodiment, a present bronchus diameter smaller than the reference bronchus diameter is set as a first condition in recording predetermined information including a VBS image.

In the present embodiment, the image processing section 25 includes an image-change-amount detecting section 25g functioning as image-change-amount detecting means for detecting a change amount of a feature section in an endoscopic image (also simply referred to as image) picked up by the image pickup apparatus 16.

In this way, the present embodiment includes the bronchus-diameter-change-amount detecting section 25e functioning as first change-amount detecting means and the image-change-amount detecting section 25g functioning as second change-amount detecting means. The bronchus-diameter-change-amount detecting section 25e functioning as the first change-amount detecting means is used for detecting (determining) whether the first condition is satisfied.

The image-change-amount detecting section 25g functioning as the second change-amount detecting means is used for detecting whether a second condition that the change amount of the feature section in the endoscopic image is larger than a set value ΔDth is satisfied. In the present embodiment, information including the VBS image is recorded when the second condition is further satisfied (a predetermined condition is satisfied) in a state in which the first condition is satisfied.

The image-change-amount detecting section 25g includes a bronchus-diameter-change-amount detecting section 25h that detects a change amount of a bronchus diameter (an inner diameter of the bronchus 2) serving as the feature section, a brightness-change-amount detecting section 25i that detects a change amount of brightness in a branch region or a change amount of brightness of a feature region in the branch region, and a shape-change-amount detecting section 25j that detects a shape change amount in the branch region or a shape change amount of a feature section in the branch region.

The shape-change-amount detecting section 25j includes a spur-change-amount detecting section 25k that detects, as the shape change amount of (the feature section in) the branch region, a change amount of length or an angle of a spur (a branch point or a branch boundary) where the lumen of the bronchus 2 divides (branches). The brightness-change-amount detecting section 25i has a function of a visual-field-defect detecting section 25l explained below. The function of the visual-field-defect detecting section 25l is not limitedly included in the brightness-change-amount detecting section 25i.

Note that the control section 26 may correct route data generated (before insertion of the insertion section 11 of the endoscope 3A) by the route-data generating section 29a according to the position of the distal end of the insertion section 11 estimated by the position estimating section 25c.

The control section 26 has a function of a condition determining section 26b that performs determination concerning whether a detection result by the bronchus-diameter-change-amount detecting section 25e and a detection result by the image-change-amount detecting section 25g satisfy a predetermined condition for recording.

When determining that the predetermined condition is satisfied, the condition determining section 26b in the control section 26 causes the information recording section 27 to record, (as candidate information presented in re-alignment), information concerning a position and a posture of the distal end of the insertion section 11 estimated by the position estimating section 25c when it is determined that the predetermined condition is satisfied and predetermined information in which a VBS image corresponding to the information concerning the position and the posture is associated with the information, that is, position and image information.

Therefore, the information recording section 27 has a function of information recording means for recording, on the basis of the detection result by the bronchus-diameter-change-amount detecting section 25e and the detection result by the image-change-amount detecting section 25g, the predetermined information serving as the candidate information in which the information concerning the position and the posture of the distal end of the insertion section 11 and the VBS image corresponding to the information concerning the position and the posture are associated with each other.

The condition determining section 26b of the control section 26 has a function of an information-recording control section 26c functioning as information-recording control means for performing control for recording predetermined information in the information recording section 27. When the bronchus diameter detected by the bronchus-diameter-change-amount detecting section 25e functioning as the lumen-diameter-change-amount detecting means is smaller than the reference bronchus diameter and the change amount of the feature section of the spur or the like detected by the image-change-amount detecting section 25g changes more than the set value, the information-recording control section 26c controls the information recording section 27 to record predetermined information including the VBS image. Note that, instead of the condition determining section 26b in the control section 26 performing the determination concerning whether the detection result by the bronchus-diameter-change-amount detecting section 25e and the detection result by the image-change-amount detecting section 25g satisfy the predetermined condition for recording, the bronchus-diameter-change-amount detecting section 25e and the image-change-amount detecting section 25g may respectively perform determinations concerning whether the first condition and the second condition are satisfied. Therefore, the image processing section 25 may be configured to include the function of the condition determining section 26b.

When an instruction signal for performing re-alignment is inputted from the input apparatus 31 in order to perform the re-alignment, for example, when the surgeon thinks that accuracy of a present estimated position of the distal end of the insertion section 11 is low, for example, the display control section 26a of the control section 26 reads out predetermined information recorded in the information recording section 27 and controls the predetermined information to be displayed on the monitor 32 as candidate information via the image processing section 25.

In this case, the image processing section 25 includes the image generating section 25d that generates an image in which the candidate information read out from the information recording section 27 is displayed to be superimposed on the bronchus shape image 2a. More specifically, the image processing section 25 displays a position and a posture of the distal end of the insertion section 11 and a VBS image corresponding to the position and the posture to be superimposed on the bronchus shape image 2a. Note that, as explained below, FIG. 2D shows a state in which, on the bronchus shape image 2a displayed on the monitor 32, a position of the distal end of the insertion section 11 is displayed in a position corresponding to the position and a VBS image corresponding to the position is superimposed and displayed in the position by associating the VBS image with the position (by a line).

The surgeon performs re-alignment with reference to the candidate information. The alignment processing section 25a or the position estimating section 25c can acquire information concerning the position and the posture of the distal end of the insertion section 11 in a state in which the information is associated with the coordinate system (the CT coordinate system) of the bronchus 2. According to the re-alignment, the position estimating section 25c can secure predetermined accuracy and perform operation for inserting the distal end of the insertion section 11 into the depth side of the bronchus 2 again from a re-aligned position.

In the present embodiment, as explained above, in the case of a determination result that the detection result by the bronchus-diameter-change-amount detecting section 25e satisfies the first condition and the detection result by the image-change-amount detecting section 25g satisfies the second condition (i.e., the predetermined condition including the first condition and the second condition is satisfied), predetermined information including a (estimated) position and a posture of the distal end of the insertion section 11 in the case in which the determination result is obtained and a VBS image corresponding to the position and the posture is recorded in the information recording section 27 as candidate information. Note that the predetermined information serving as the candidate information may be recorded in the information recording section 27 to include at least the position in the position and the posture of the distal end.

When the re-alignment is performed by recording the predetermined information (also simply referred to as information) when a plurality of conditions different from each other are satisfied, a proper information amount (or the number) of candidate information can be displayed (or presented) on the monitor 32 functioning as the display means.

In the present embodiment, a change amount of a feature section of a bronchus diameter or the like concerning the bronchus 2 set as the predetermined lumen organ in the endoscopic image picked up by the image pickup apparatus 16 is detected by the image-change-amount detecting section 25g. Predetermined information including (information concerning) a position and a posture of the distal end of the insertion section 11 in the detection result and predetermined information including a VBS image corresponding to the position and the posture is recorded in the information recording section 27 (as candidate information presented when the re-alignment is performed).

The user such as the surgeon can easily grasp a condition or a situation of recording of information because the user performs operation for inserting the insertion section 11 while observing the endoscopic image picked up by the image pickup apparatus 16. The candidate information presented when the re-alignment is performed can be easily set to candidate information with which a change amount in the feature section in the endoscopic image sensitively changes with respect to movement of the position of the distal end of the insertion section 11. Therefore, alignment by image comparison can also be easily performed.

Note that although the information recorded in the information recording section 27 includes the position and the posture of the distal end of the insertion section 11 and the VBS image corresponding to the position and the posture, the information may be recorded to further include an endoscopic image corresponding to the information concerning the position and the posture.

The image processing section 25 includes an image memory 25f for temporarily storing the endoscopic image and the VBS image and used as a work area of image processing when comparing both of the endoscopic image and the VBS image and performing the image matching. Note that an image memory 25f may be provided on the outside of the image processing section 25.

In the present embodiment, for example, the input apparatus 31 may be configured to include a designating section 31a that selectively designates (or sets) each of the first condition concerning the change amount of the inner diameter of the bronchus 2 detected by the bronchus-diameter-change-amount detecting section 25e and the second condition concerning a change amount of the feature section detected by the image-change-amount detecting section 25g.

For example, the information recording section 27 may include a condition-information recording section 27a that, besides recording the predetermined information (the position and image information) serving as the candidate information, records condition information of the first condition and condition information of the second condition in advance. Note that the condition-information recording section 27a may be provided separately from the information recording section 27.

The condition information of the first condition is (a) a difference value (a change amount) between a reference bronchus diameter Dre set in advance and a present bronchus diameter Da (at the distal end of the insertion section 11) and (b') (an amount of change of) a difference value between the reference bronchus diameter Dre and a present bronchus diameter in a reference position set by the user such as the surgeon. Note that (b') may be further subdivided into (b) a difference value (a change amount) between the bronchus diameter Dre of a brunching section of the number of branches set in advance and the present bronchus diameter Da, (c) (a change amount of) a difference value between the reference bronchus diameter Dre and the present bronchus diameter Da in any position set by the user, and (d) a difference value (a change amount) between the reference bronchus diameter Dre and the present bronchus diameter Da in a position of a distal end of an endoscope having endoscope insertion length set in advance.

The condition information of the second condition is, for example, (a) a change in the bronchus diameter (the bronchus diameter calculated from the endoscopic image) Den in the endoscopic image, (b) a change in brightness of the endoscopic image or a display screen on which the endoscopic image is displayed, (c) a change in a shape of a branch in the endoscopic image, (d) a change in length of a spur in the endoscopic image, (e) a change in an angle of the spur in the endoscopic image, (f) a defect of a visual field (in the endoscopic image), (g) a large blur of the endoscopic image, and (h) a change in which something other than the bronchus is reflected on the endoscopic image. The user such as the surgeon may be enabled to selectively designate, for example, from a designating section 31a (of the input apparatus 31), a condition out of the condition information of the first condition in (a) to (d) and the condition information of the second condition in (a) to (h).

In this case, the control section 26 has a function of a condition setting section 26d that performs setting of the first condition and the second condition according to the designation by the designating section 31a.

When performing the setting of the first condition and the second condition, the condition setting section 26d may also perform setting of threshold information and the like used when the condition determining section 26b performs the determination. Note that the threshold information may also be recorded in the information recording section 27 in association with information concerning the first condition and the second condition. Only the condition information of one condition (e.g., the second condition) in the information concerning the first condition and the second condition may be recorded in the condition-information recording section 27a.

In the present embodiment, the control section 26 includes the display control section 26a that performs control to, when the position estimating section 25c functioning as the position-information acquiring means fails in acquisition of position information of the distal end of the insertion section 11 based on a comparison result of the image comparing section 25b or when an instruction signal for presenting, as candidate information, predetermined information recorded in the information recording section 27 is generated, display a position of the distal end of the insertion section 11 in the predetermined information recorded in the information recording section 27 in a corresponding position in the bronchus shape image 2a and display a corresponding VBS image in the position of the distal end. The position estimating section 25c or the alignment processing section 25a acquires position information of the distal end of the insertion section 11 through comparison of the VBS image read out from the information recording section 27 and a present endoscopic image picked up by the image pickup means.

Note that, in FIG. 1, for example, the image processing section 25 can be configured by a CPU (central processing unit). The alignment processing section 25a to the image-change-amount detecting section 25g inside the image processing section 25 may be respectively configured using dedicated hardware other than the CPU. The control section 26 shown in FIG. 1 may be configured by a CPU or dedicated hardware other than the CPU.

The endoscope system 1 having such a configuration includes the CT-image-data recording section 22 functioning as the image recording means for recording three-dimensional image information in the object acquired in advance, the bronchus extracting section 23 functioning as lumen-organ extracting means for extracting the bronchus 2 set as the predetermined lumen organ from the three-dimensional image information, the VBS-image generating section 24 functioning as the virtual-endoscopic-image generating means for generating an endoscopically-drawn virtual endoscopic image from a predetermined visual point position with respect to information concerning the predetermined lumen organ extracted by the lumen-organ extracting means, the image pickup apparatus 16 or 16' functioning as the image pickup means provided in the endoscope 3A or 3B and for picking up an image of the predetermined lumen, the position estimating section 25c functioning as the position-information acquiring means for acquiring position information of the distal end of the insertion section 11 of the endoscope 3A in the predetermined lumen organ, the bronchus-diameter-change-amount detecting section 25e functioning as the lumen-diameter-change-amount detecting means for detecting, on the basis of the position information of the distal end of the insertion section of the endoscope 3A or 3B, a change amount of the lumen diameter of the bronchus 2 set as the predetermined lumen organ, the image-change-amount detecting section 25g functioning as the image-change-amount detecting means for detecting, in an endoscopic image picked up by the image pickup means, a change amount of the feature section concerning the bronchus 2 set as the predetermined lumen organ, and the information recording section 27 functioning as the information recording means for recording, on the basis of a detection result of the lumen-organ-change-amount detecting means and a detection result of the image-change-amount detecting means, predetermined information including a position of the distal end of the insertion section of the endoscope and the virtual endoscopic image corresponding to the position of the distal end.

Figure 4:
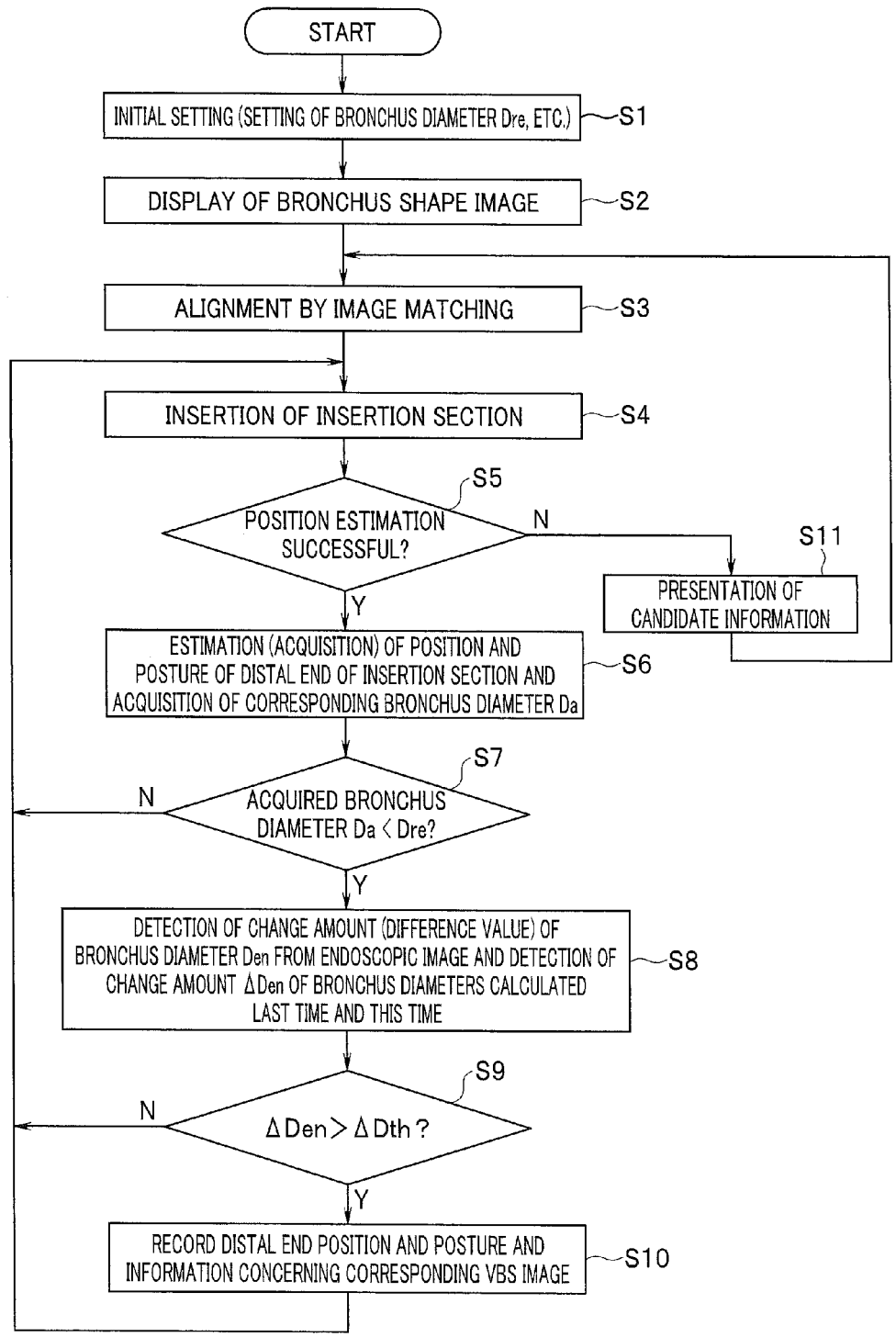
FIG. 4 is a flowchart for explaining an example of processing content in the first embodiment.

The operation of the present embodiment is explained. FIG. 4 shows representative processing in the present embodiment.

When a power supply of the endoscope system 1 shown in FIG. 1 is turned on and the endoscope apparatus 4A (or 4B) and the insertion supporting apparatus 5 change to an operation state, the processing shown in FIG. 4 is started. Processing of initial setting is performed in first step S1 in FIG. 4. As the processing of the initial setting, the surgeon inputs, from the input apparatus 31, information used for insertion support in the present embodiment. In this case, the surgeon performs designation of a first condition and a second condition from the designating section 31a. The condition determining section 26b changes to a state in which the condition determining section 26b performs determination corresponding to the designated first and second conditions.

A case in which the surgeon (a) designates a difference value between the bronchus diameter (the reference bronchus diameter) Dre set in advance and the present bronchus diameter Da as the first condition and designates a change in the bronchus diameter Den in an endoscopic image as the second condition is represented as (A) and explained below.

(A) When the Difference Value Between the Reference Bronchus Diameter Dre Set in Advance and the Present Bronchus Diameter Da and the Change (a Change Amount) in the Bronchus Diameter Den in the Endoscopic Image are Designated In the case of (A) above, in the present embodiment, predetermined information is recorded when the present bronchus diameter Da satisfies a condition that the present bronchus diameter Da is smaller than the set reference bronchus diameter Dre and when a change amount ΔDen of the bronchus diameter Den calculated from the endoscopic image changes to a threshold or a set value ΔDth set in advance.

By setting the reference bronchus diameter Dre, it is possible to record, without performing recording of information in an insertion region such as a vicinity of the entrance of the bronchus 2 not requiring recording, desired information in an insertion region that the surgeon desires to record. The insertion region such as the vicinity of the entrance of the bronchus 2 is a region where a bronchus diameter is large and the surgeon can easily operate the insertion section 11 as intended. Therefore, the surgeon can easily grasp where in the bronchus 2 the position of the distal end of the insertion section 11 is present. Further, since the insertion region is a region near a position where first alignment is performed, the surgeon can accurately perform estimation of a position of the distal end of the insertion section 11.

On the other hand, in a region on a periphery side to a certain degree of the bronchus 2, it is difficult to perform insertion of the insertion section 11 and the bronchus 2 decreases in a diameter. Therefore, it tends to be difficult to see where in the bronchus 2 the position of the distal end is present. Further, since the region is a lumen region a distance apart from the position where the first alignment is performed, in the region, accuracy of position estimation tends to be deteriorated.

Therefore, the surgeon sometimes wants to have information used as candidate information for performing re-alignment. In such a case, the surgeon sets the reference bronchus diameter Dre equivalent to a bronchus diameter in a region that the surgeon desires to record. As explained below, the surgeon is enabled to record only predetermined information that is effective candidate information for making it easy to perform the re-alignment in a lumen region that the surgeon desires to record as explained below.

Information is recorded when the change amount ΔDen of the bronchus diameter Den in the endoscopic image changes the set value ΔDth or more. Therefore, when the re-alignment is performed by comparison of images, an image portion having a large change amount in the endoscopic image can be set in a main comparison target portion. By setting the comparison target portion having the large change amount, the surgeon is enabled to easily visually perform the re-alignment by the image comparison and the re-alignment in a short time.

When the setting of step S1 is performed as explained above, in step S2, the bronchus-shape-image generating section 23a generates, (from three-dimensional data of a patient before a test), the bronchus shape image 2a serving as a shape image of the bronchus 2 as shown in FIG. 2A. The bronchus shape image 2a is outputted to the monitor 32 through the image processing section 25. The bronchus shape image 2a is displayed on the monitor 32 as shown in FIG. 2A. The core line 35 passing the center of the lumen of the bronchus 2 is displayed on the bronchus shape image 2a as explained above. Respective positions of the core line 35 and a branch point Bi are known three-dimensional positions specified in the CT coordinate system.

In the next step S3, the surgeon inserts the insertion section 11 of the endoscope 3A into the bronchus 2. In this case, in a known position such as the entrance of the bronchus 2, the surgeon performs, using the image comparing section 25b, alignment processing by image matching such that an endoscopic image by the image pickup apparatus 16 (or 16') and a VBS image coincide with each other under a set condition (within an error with which predetermined accuracy can be secured). When the image pickup apparatus 16' is used, one endoscopic image by one image pickup apparatus 16a or 16b in the image pickup apparatus 16' only has to be adopted. Note that steps S2 and S3 may be interchanged in order or may be performed in parallel.

After the alignment processing in step S3, as shown in step S4, the surgeon inserts the distal end of the insertion section 11 further to the depth side of the bronchus 2 than an aligned position.

When the insertion section 11 is inserted, as shown in step S5, the position estimating section 25c of the image processing section 25 determines whether a position and a posture of the distal end of the insertion section 11 are successfully estimated by the image matching using the image comparing section 25b at a fixed time interval or the like.

When the position and the posture of the distal end of the insertion section 11 can be estimated by the image matching, as shown in step S6, the estimated position and the estimated posture of the distal end of the insertion section 11 are acquired and, at the same time, information concerning the bronchus diameter Da corresponding to a (present) position of the distal end of the insertion section 11 is acquired (from the CT-image-data recording section 22, the bronchus extracting section 23, or the like).

These kinds of information are temporarily stored in, for example, the image memory 25f and referred to when necessary in the processing shown in FIG. 4. Note that in the estimation of the position and the posture of the distal end of the insertion section 11 in step S6, the bronchus diameter Den may be simultaneously calculated from the endoscopic image.

The estimated position of the distal end of the insertion section 11 is displayed on the bronchus shape image 2a. As shown in FIG. 2A, an estimated position Pj is displayed in a relevant position on the bronchus shape image 2a.

In step S7 after step S6, the bronchus-diameter-change-amount detecting section 25e or the condition determining section 26b of the control section 26 determines whether the bronchus diameter Da acquired in step S5 is smaller than the reference bronchus diameter Dre set in advance. When the acquired present bronchus diameter Da is not smaller than the reference bronchus diameter Dre, the processing returns to the processing in step S4 and the surgeon inserts the insertion section 11 to the depth side.

On the other hand, when the acquired bronchus diameter Da is smaller than the reference bronchus diameter Dre in the determination processing in step S7 in FIG. 4, in step S8, (the bronchus-diameter-change-amount detecting section 25h of) the image-change-amount detecting section 25g detects (calculates) the change amount (the difference value) ΔDen of the bronchus diameter Den calculated from the endoscopic image.

That is, the image-change-amount detecting section 25g calculates the change amount ΔDen between the bronchus diameter Den calculated from the endoscopic image in the present position of the distal end of the insertion section 11 and the bronchus diameter Den calculated from the endoscopic image in a position of the distal end of the insertion section 11 estimated last time.

Note that the bronchus diameter Den calculated from the endoscopic image includes a bronchus diameter in a case of a noncircular shape widening in a direction branching in a branch section rather than an average value of the lumen of the bronchus 2. Therefore, the bronchus diameter Den calculated from the endoscopic image could be sometimes larger than the reference bronchus diameter Dre of a substantially circular shape of the lumen of the bronchus 2.

In the next step S9, the condition determining section 26b of the control section 26 determines whether the change amount ΔDen of the bronchus diameter is larger than the set value ΔDth. When the change amount ΔDen of the bronchus diameter is not larger than the set value ΔDth, the processing returns to the processing in step S4.

On the other hand, when the change amount ΔDen of the bronchus diameter is larger than the set value ΔDth, the processing proceeds to processing in the next step S10. The condition determining section 26b records, (as candidate information to be presented), predetermined information concerning a position and a posture of the distal end of the insertion section 11 corresponding to a determination result in step S9 and a VBS image corresponding to the position and the posture in the information recording section 27. After the recording of the information in step S10, the processing returns to the processing in step S4. Note that, in step S9, the condition determining section 26b may determine whether the change amount ΔDen of the bronchus diameter is the set value ΔDth or more instead of determining whether the change amount ΔDen of the bronchus diameter is larger than the set value ΔDth.

Figure 2B:
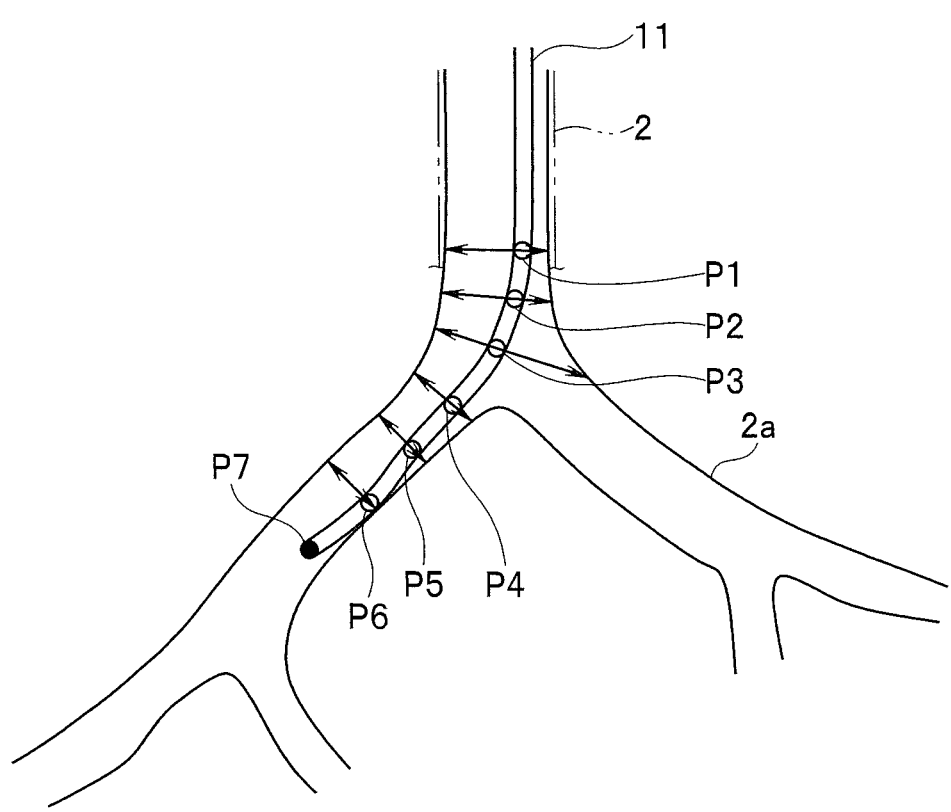
FIG. 2B is a diagram showing a state in which an endoscope is inserted into the bronchus and a bronchus diameter is calculated over time.

FIG. 2B shows a state in which the bronchus diameter Den is acquired from the endoscopic image simultaneously with the position estimation after the distal end of the insertion section 11 changes to a state in which the distal end satisfies the first condition, that is, the condition in step S7 as shown in FIG. 2A.

As shown in FIG. 2B, the position Pj of the distal end of the insertion section 11 (in FIG. 2B, j=1, 2, . . . , and 6) is estimated and acquired by the position estimating section 25c, for example, at every fixed time interval. The estimated position Pj moves to a present position P7 of the distal end through positions P1, P2, . . . , and P6. Note that the position Pj is not limitedly acquired at every fixed time interval and may be acquired at every fixed distance, when calculation of estimation of a distal end position of the insertion section 11 is performed, may be performed every predetermined number of times of the calculation, and, when the calculation for calculating a bronchus diameter is performed, may be performed every predetermined number of times of calculation or the like.

The respective positions Pj indicated by white circles in FIG. 2B are positions where the first condition (step S7) is satisfied and the position P7 indicated by a black circle is a present position.

Figure 2C:
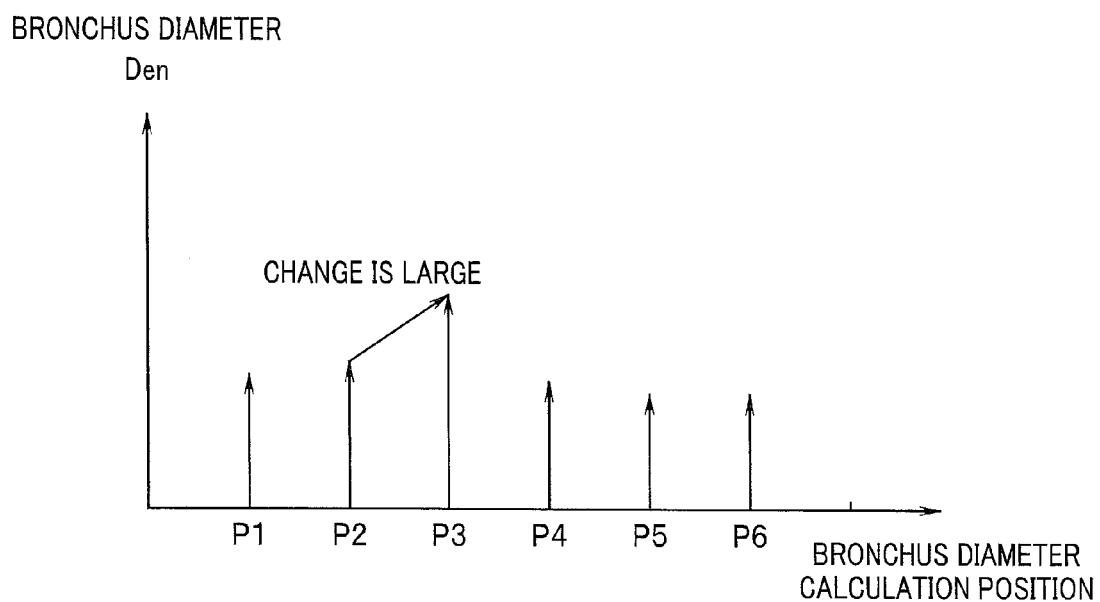
FIG. 2C is a diagram showing positions where the bronchus diameter is calculated and sizes of the calculated bronchus diameter.
Figure 2D:
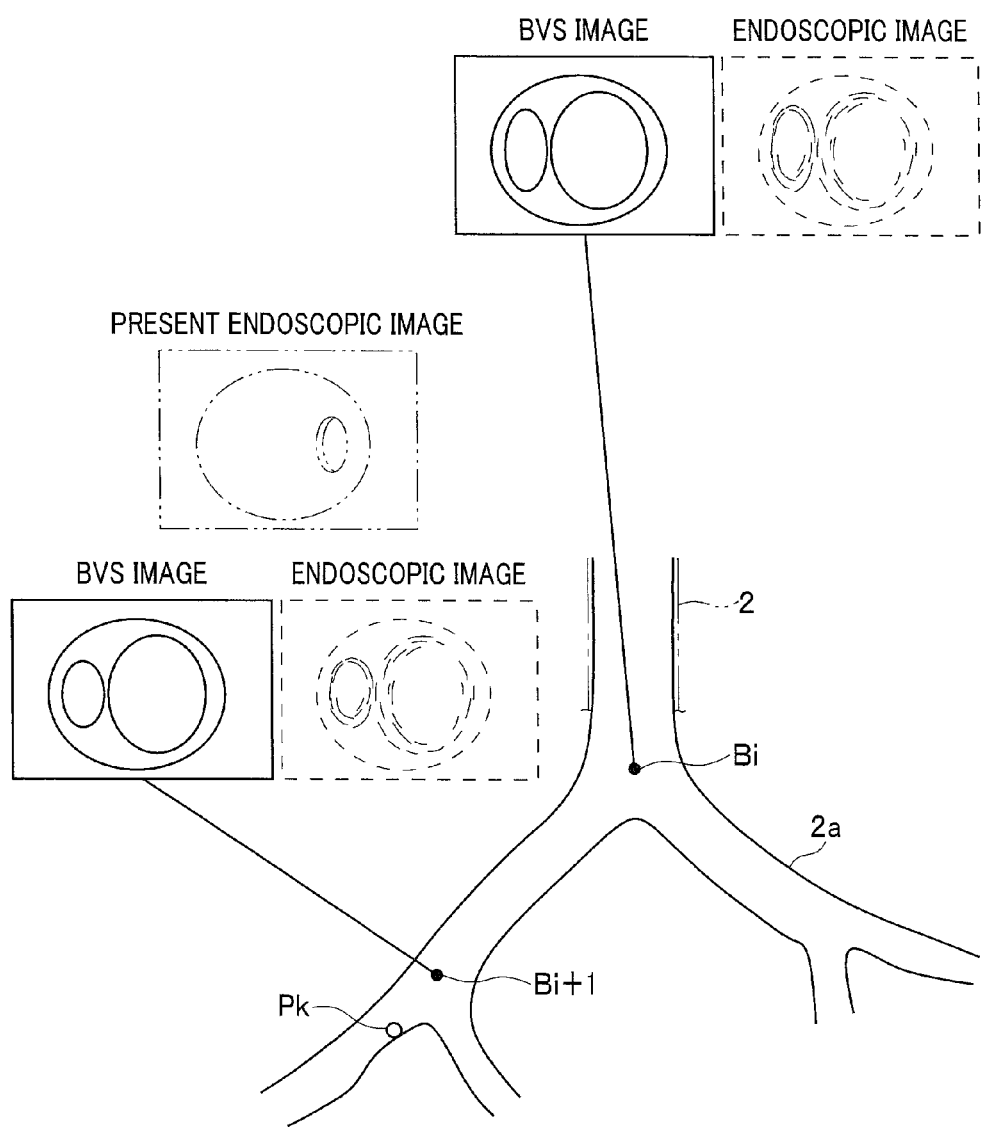
FIG. 2D is a diagram showing candidate information displayed on a monitor when an instruction for performing re-alignment is given.

An overview of a state of a change in the bronchus diameter Den calculated by the measurement operation section 18d or the like in the respective positions Pj is as shown in FIG. 2B. FIG. 2C shows the positions P1 to P6 where the bronchus diameter Den is calculated and a state of a change in the calculated bronchus diameter Den during movement of the distal end of the insertion section 11 in a state in which step S7 is satisfied. Note that information acquired at the respective positions P1 to P6 is temporarily stored in the image memory 25f or the like and used for comparison.

As shown in FIG. 2B and FIG. 2C, the bronchus diameter Den greatly changes to be peaked near the branch point Bi. Therefore, when the distal end of the insertion section 11 moves from the position P2 to the position P3, the change amount ΔDen of the bronchus diameter Den changes from a state in which the change amount ΔDen is smaller than the set value ΔDth to a large value exceeding the set value ΔDth.

Therefore, when the position P2 changes to the position P3, the condition determining section 26b records predetermined information concerning a VBS image corresponding to a position and a posture in P3 in the information recording section 27 (as candidate information) together with, for example, a position and a posture of the position P3.

Note that when the position Pj changes from the position P3 to the position P4, the bronchus diameter Den also changes from a large value to a small value. However, since the bronchus diameter Den is recorded in the position P3, the bronchus diameter Den is not recorded in the position P4. Instead of recording the information concerning the corresponding VBS image in the information recording section 27 (as the candidate information) together with the position and the posture of P3, the condition determining section 26b may record the information concerning the corresponding VBS image together with information concerning a position and a posture between P2 and P3.

As in the case of the position P3 (substantially a position of the branching point Bi), information may be set to be selectively recorded near a position where the bronchus diameter Den is maximized or peaked in the endoscopic image. When the information is recorded in this way, a change in a portion equivalent to the bronchus diameter Den in the endoscopic image in the case in which the candidate information is presented and the distal end of the insertion section 11 is moved for the re-alignment is large. Therefore, it is easy to perform alignment by image matching (image comparison) (candidate information shown in FIG. 2D explained below is equivalent to an example in which information is recorded near positions of branching points Bi and Bi+1 where the bronchus diameter Den is maximized or peaked).

When performing the alignment, the surgeon pays attention to a bronchus diameter Den portion in the endoscopic image and adjusts the position and the posture of the distal end of the insertion section 11 such that bronchus diameter Den portion is maximized. When the re-alignment is performed in this way, adjustment content (an adjustment policy) is clarified such that a portion that should be paid attention is easily grasped and a value of the portion is maximized. Therefore, it is easy to perform the alignment by the image matching (image comparison).

On the other hand, in the related art, a portion that should be noted is unclear and an orientation concerning how the position and the posture of the distal end of the insertion section 11 should be adjusted with respect to a change in the position and the posture is also unclear. Therefore, the re-alignment takes time.

According to the alignment in step S3 explained above, when a moving distance from the aligned position is small, the position estimating section 25c can relatively accurately perform position estimation. However, when the moving distance increases, accuracy of the position estimation is sometimes deteriorated.

When the position estimation is unsuccessful in step S5 in some case, in step S11, the display control section 26a of the control section 26 reads out the predetermined information stored in the information recording section 27 and sends the predetermined information to the image processing section 25. The image processing section 25 outputs an image signal for presented information to the monitor 32. The monitor 32 presents the candidate information. The processing returns to the processing in step S3.

In step S3, the surgeon performs the re-alignment with reference to the candidate information displayed on the monitor 32. After the re-alignment is performed, the processing of FIG. 4 is repeatedly performed. In this way, it is possible to smoothly perform operation for inserting the insertion section 11 into the periphery side (the depth side) of the bronchus 2.

FIG. 2D shows a display example of the candidate information in the case of step S11. In the display example of the candidate information shown in FIG. 2D, positions of the distal end of the insertion section 11 recorded in the information recording section 27 up to a position Pk (the branch points Bi and Bi+1 near a position where the change amount ΔDen of the bronchus diameter Den is maximized) and VBS images respectively corresponding to the positions are displayed to be connected by, for example, a line. Note that a branch point Bi−1 and the like on a base side (an insertion port side) with respect to the branch point Bi may be displayed in the same manner.

Predetermined information respectively recorded near the branch points Bi and Bi+1 where the lumen, which is a characteristic region, in the bronchus 2 branches as shown in FIG. 2D is displayed as candidate information in the case in which the re-alignment is performed. The candidate information narrowed down to a necessary minimum near the branch points suitable for the re-alignment is displayed in this way. Therefore, the surgeon can easily perform the re-alignment smoothly and in a short time. In other words, information to be recorded is narrowed down according to the first condition and the second condition. Therefore, it is possible to record predetermined information of an information amount suitable for performing the re-alignment.

Note that, in FIG. 2D, a presentation example of the candidate images at the branch points Bi and Bi+1 is shown. However, for the position Pk of the distal end of the insertion section 11, information recorded in the information recording section 27 in an estimated state closest to the position Pk may be presented as candidate information. When the present embodiment is applied to FIG. 2D, only information recorded near the branch point Bi+1 may be presented as the candidate information.

On the other hand, in the related art, information to be recorded is not narrowed down. Therefore, candidate information displayed in the re-alignment is excessive or insufficient. It takes time until the re-alignment is performed with an appropriate amount of candidate information.

In the present embodiment, information is recorded when the feature section in the endoscopic image greatly changes with respect to the movement of the position of the distal end of the insertion section 11. Therefore, the user such as the surgeon can easily grasp a condition for recording the information. Therefore, in the present embodiment, it is possible to record predetermined information of an information amount suitable for performing the re-alignment under a condition that the user can easily grasp visually.

In the present embodiment, when the recorded information is displayed (presented) as the candidate information to perform the re-alignment, a characteristic that the feature section in the endoscopic image greatly changes is reflected on the movement of the position of the distal end of the insertion section 11. Therefore, the user can easily perform the re-alignment visually by the image matching.

When the information in the state of the position P3 where the bronchus diameter Den is maximized (peaked) with respect to a track of the movement of the position of the distal end is recorded in the information recording section 27, the re-alignment can be easily performed. Note that, on the monitor 32, as further indicated by an alternate long and two short dashes line in FIG. 2D, a present endoscopic image may be displayed as a combined image superimposed on the bronchus shape image 2a together with the VBS image (and the endoscopic image) serving as the candidate information read out from the information recording section 27 and displayed. When the present endoscopic image is displayed adjacent to the candidate information in this way, the alignment by the image comparison with the candidate information can be easily performed.

In this case, an image moving section that makes it possible to move a display position of the VBS image on the candidate information side to be superimposed on a display position of the present endoscopic image and makes it possible to move a display position of the endoscopic image on the candidate information side to be superimposed on a display position of the present endoscopic image may be provided in the image processing section 25. Alternatively, the image processing section 25 may include an image moving section that makes it possible to move the display position of the present endoscopic image to the display position of the VBS image on the candidate information side and the display position of the endoscopic image on the candidate information side.

Figure 5:
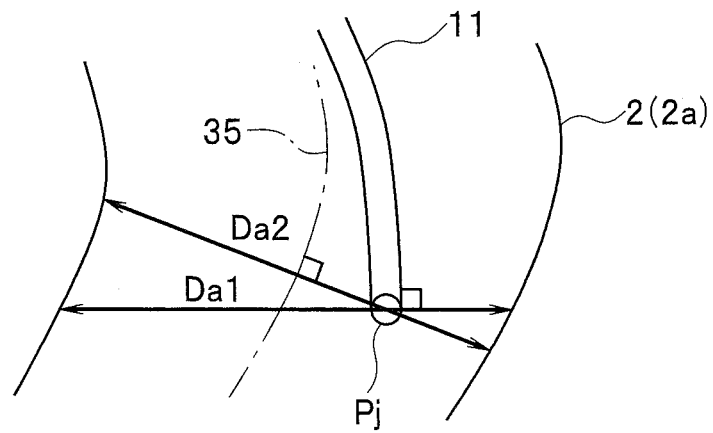
FIG. 5 is an explanatory diagram of a case in which the bronchus diameter is acquired.
Figure 6:
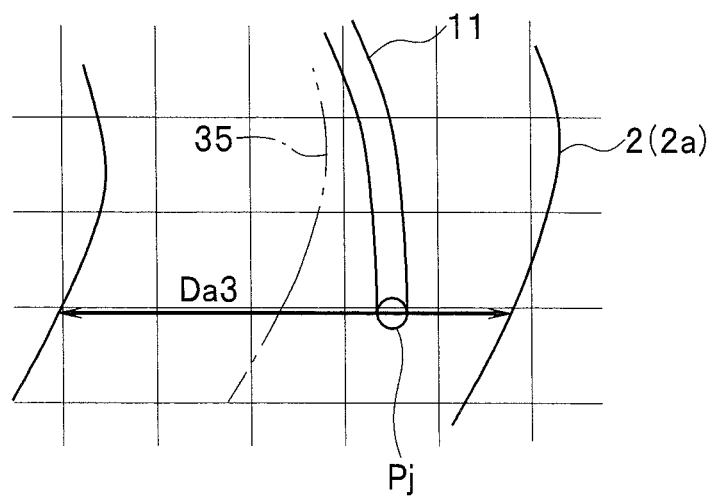
FIG. 6 is an explanatory diagram of a case in which the bronchus diameter is acquired by a method different from a method shown in FIG. 5.

Note that when the bronchus-diameter-change-amount detecting section 25e acquires the bronchus diameter Da on the basis of the information concerning the position of the distal end of the insertion section 11, the bronchus-diameter-change-amount detecting section 25e may acquire the bronchus diameter Da according to methods shown in FIG. 5 and FIG. 6.

When a bronchus diameter is acquired (measured), a bronchus diameter Da1 calculated from the lumen of the bronchus 2 on a surface perpendicular to a longitudinal direction (or an axial direction) of the distal end of the insertion section 11 as shown in FIG. 5 may be adopted. A bronchus diameter Da2 calculated along a surface perpendicular to the core line 35 to include the distal end of the insertion section 11 and a perpendicular reaching the core line 35 from the distal end may be adopted. Alternatively, Da3 in a direction of a coordinate axis of the CT coordinate system for managing three-dimensional data of the bronchus 2 as shown in FIG. 6 may be adopted. In other words, the bronchus-diameter-change-amount detecting section 25e may detect, on the basis of the information concerning the position of the distal end of the insertion section 11, a change amount of a lumen diameter of the predetermined lumen organ on the surface perpendicular to the longitudinal direction of the distal end or may detect a change amount of the lumen diameter of the predetermined lumen organ on the surface perpendicular to the core line 35, which is a center line of the lumen of the bronchus 2.

In the case of (A) explained above, one reference bronchus diameter Dre used for the first condition is set irrespective of a patient. On the other hand, in cases (B), (C), and (D) explained below, for the purpose of setting an optimum reference bronchus diameter for each patient, a reference bronchus diameter is set for each patient as explained below.

(B) A Bronchus Diameter of Branch Sections of the Number of Branches Set in Advance In performing the re-alignment, the surgeon performs setting for determining in advance and inputting branch sections of the number of branches that the surgeon considers it desirable to record as candidate information to be referred to. Note that the number of branches is identification information added to be easily specified by, for example, being sequentially numbered according to order of branch sections serving as portions where the lumen branches from an entrance in the bronchus. A bronchus diameter corresponding to the number of branches set in advance by the surgeon is calculated from three-dimensional data of the bronchus extracting section 23 or the CT-image-data recording section 22 and the calculated bronchus diameter is set as the reference bronchus diameter Dre.

After the setting, an operation same as the operation in the case of (A) is performed using the set reference bronchus diameter Dre.

Consequently, the reference bronchus diameter Dre can be set according to a bronchus of an actual patient. Therefore, even in the case of patients having different physiques or the like, it is possible to appropriately set the reference bronchus diameter Dre corresponding to a bronchus of a patient into which the insertion section 11 is actually inserted.

The surgeon can accurately set the reference bronchus diameter Dre corresponding to a bronchus diameter of a position that the surgeon desires to actually record as candidate information. Therefore, it is possible to record only effective information, which is candidate information desired by the surgeon, without unnecessarily recording information that does not need to be recorded.

Note that, as in the case of (A) explained above, one reference bronchus diameter Dre may be set and set as a condition in recording a bronchus diameter smaller than a value of the reference bronchus diameter Dre. When the number of branches set as an insertion target is determined, a second reference bronchus diameter may be set.

Specifically, two bronchus diameters, i.e., a reference bronchus diameter Dre0 corresponding to the number of branches of the reference bronchus diameter corresponding to the bronchus diameter in a position desired to be recorded as explained above and a reference bronchus diameter Dre1 corresponding to the bronchus diameter of the number of branches set as the insertion target are set. Satisfaction of a bronchus diameter between the two reference bronchus diameters Dre0 and Dre1 may be set as a condition in performing recording. In other words, besides the one reference bronchus diameter Dre set as a reference bronchus diameter on an upper limit side concerning the first condition, a reference bronchus diameter on a lower limit side may be further set. When the calculated present bronchus diameter Da is smaller than the reference bronchus diameter on the lower limit side, it may be determined that the endoscope can be inserted to a target lumen region. The recording operation may be ended.

Instead of the number of branches explained above, a degree, a name of which is anatomically determined for each branch, may be used.

Figure 7:
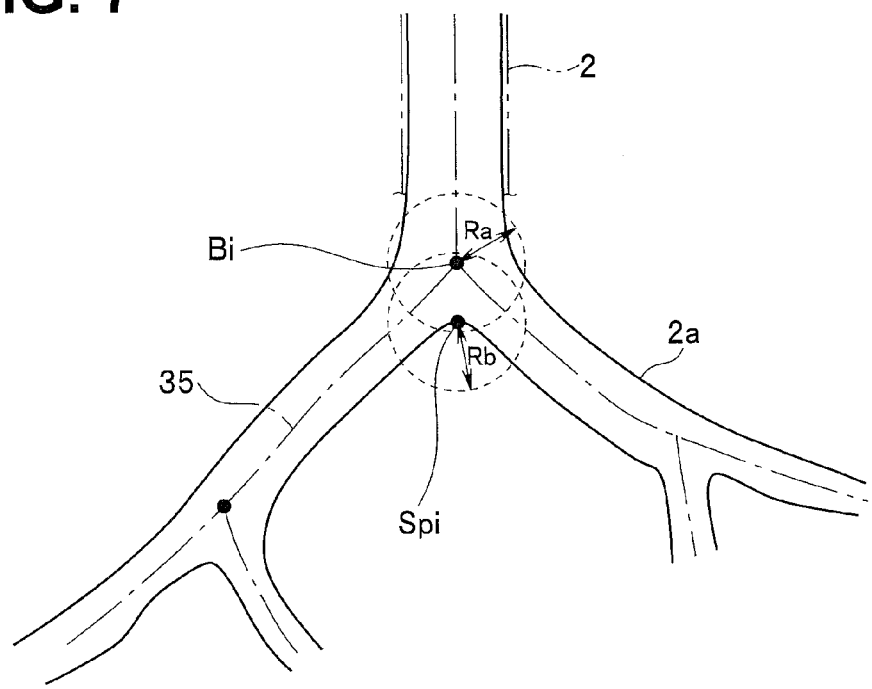
FIG. 7 is an explanatory diagram of positions where the bronchus diameter is acquired.

Note that when it is detected (calculated) whether the present bronchus diameter Da satisfies a condition that the present bronchus diameter Da is smaller than the reference bronchus diameter Dre, a position to be detected (calculated) may be set near positions of the branch point Bi and a spur Spi on the core line 35 as shown in FIG. 7. Alternatively, as indicated by a dotted line, the position to be detected (calculated) may be limited within a region of a radius Ra or Rb around the branch point Bi or the spur Spi. When such a region is set, the region may be set for each branch point Bi or each spur Spi.

Figure 8:
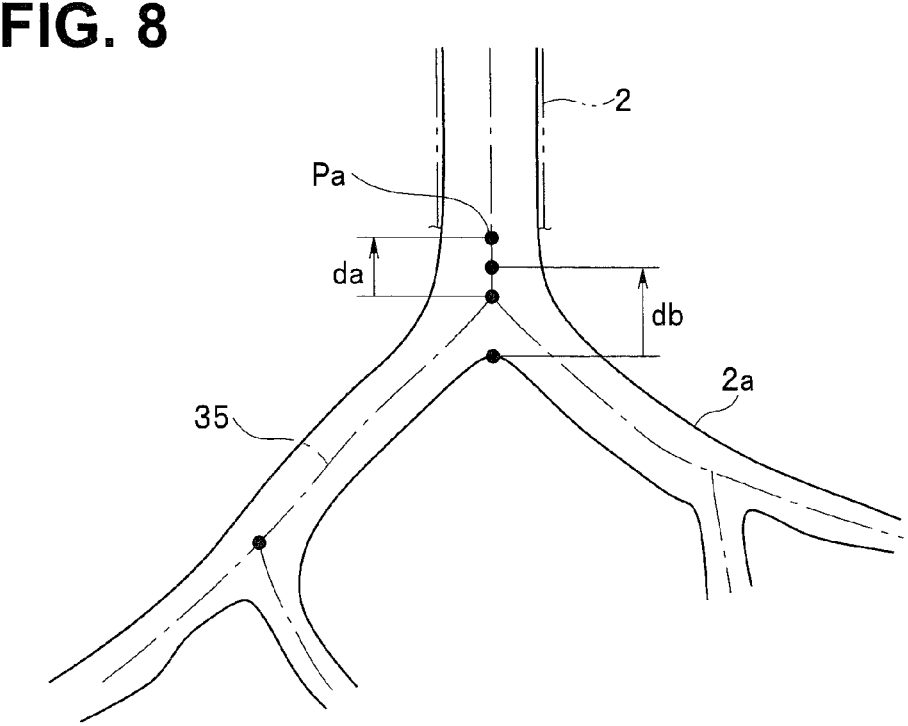
FIG. 8 is an explanatory diagram of positions where the bronchus diameter is acquired in setting different from setting shown in FIG. 7.

Unlike FIG. 7, as shown in FIG. 8, a position Pa back to the entrance (the base) side of the bronchus 2 along a direction of the core line 35 by a distance da from the branch point Bi or a position Pb back to the entrance (the base) side of the bronchus 2 along the direction of the core line 35 by the distance da from the spur Spi may be set as a position where a change in the bronchus diameter Den is detected (calculated). In this case, a position deviating from the position Pa or Pb on the core line 35 may be included in the position where a change in the bronchus diameter Den is detected (calculated).

Figure 9:
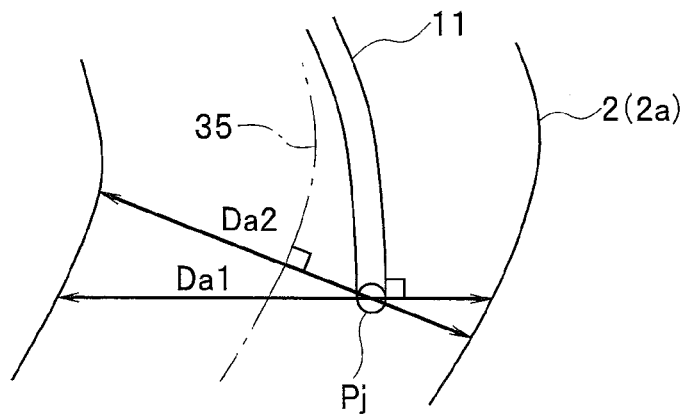
FIG. 9 is an explanatory diagram of a case in which the bronchus diameter is acquired.
Figure 10:
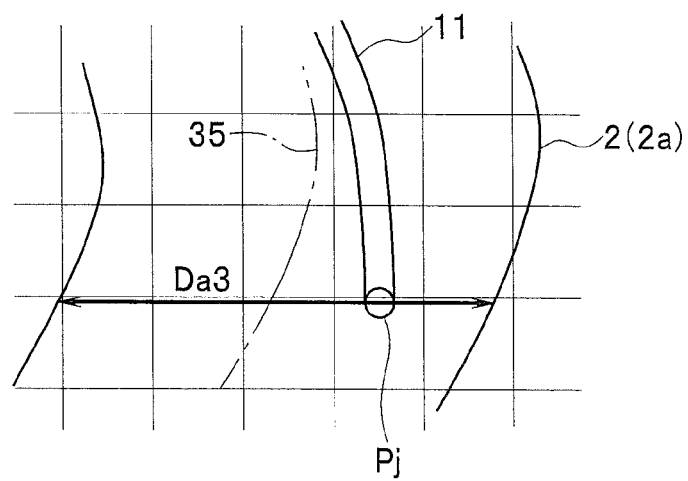
FIG. 10 is an explanatory diagram of a case in which the bronchus diameter is acquired by a method different from a method shown in FIG. 9.

As a direction in calculating the bronchus diameter in the position Pj at the distal end of the insertion section 11, as shown in FIG. 9 and FIG. 10, the bronchus diameter may be the bronchus diameter Da1 along the surface perpendicular to the axial direction of the distal end of the insertion section 11, the bronchus diameter Da2 along the surface perpendicular to the core line 35, or the bronchus diameter Da3 along the coordinate axis of the three-dimensional data of the CT coordinate system.

As a method of calculating the reference bronchus diameter Dre, a maximum/a minimum of the relevant bronchus 2, a bronchus diameter of only a right lung, a bronchus diameter of only a left lung, a bronchus diameter of both the lungs, a bronchus diameter only on an insertion route of the insertion section 11 set in advance, or the like may be calculated.

(C) A Bronchus Diameter in any Position Set by the User Such as the Surgeon

Before a test, a bronchus diameter in a position on the bronchus 2 designated by the surgeon is calculated from the three-dimensional data of the CT coordinate system. The calculated bronchus diameter is set as the reference bronchus diameter Dre. After the setting, an operation same as the operation in the case of (A) is performed using the reference bronchus diameter Dre.

As a calculation method for a bronchus diameter, as shown in FIG. 9 and FIG. 10, the bronchus diameter may be set as the bronchus diameter Da1 along the surface perpendicular to the axial direction of the distal end of the insertion section 11, the bronchus diameter Da2 along the surface perpendicular to the core line 35, or the bronchus diameter Da3 along the coordinate axis of the three-dimensional data of the CT coordinate system.

In the case of (C), there is an effect substantially same as the effect in the case of (B).

(D) The Bronchus Diameter Dre in a Position of the Distal End of the Insertion Section 11 Having Insertion Length Set in Advance The surgeon sets, from the input apparatus 31, insertion length of the insertion section 11 (endoscope insertion length) at which the surgeon considers it desirable to acquire candidate information in advance. The surgeon calculates, with, for example, a function of a distance estimating section included in the position estimating section 25c of the image processing section 25, all positions in the bronchus 2 reachable by the set insertion length in the three-dimensional data of the CT-image-data recording section 22 or the bronchus extracting section 23.

The surgeon calculates respective bronchus diameters in the calculated respective positions and sets an average of the bronchus diameters as the reference bronchus diameter Dre.

After the setting, an operation same as the operation in the case of (A) is performed. In the case of (D), there is an effect substantially same as the effect in the case of (B).

Note that as a calculation method for a bronchus diameter, as shown in FIG. 9 and FIG. 10, the bronchus diameter may be set as the bronchus diameter Da1 calculated on the surface perpendicular to the axial direction of the distal end of the insertion section 11, the bronchus diameter Da2 calculated on the surface perpendicular to the core line 35, or the bronchus diameter Da3 along the coordinate axis of the three-dimensional data of the CT coordinate system.

As a method of calculating the reference bronchus diameter Dre, a maximum/a minimum of the relevant bronchus 2, a bronchus diameter of only a right lung, a bronchus diameter of only a left lung, a bronchus diameter of both the lungs, a bronchus diameter only on an insertion route of the insertion section 11 set in advance, or the like may be calculated.

In (A) to (D) explained above, the image-change-amount detecting section 25g is the bronchus-diameter-change-amount detecting section 25h that detects a change in the bronchus diameter Den in the endoscopic image. However, the image-change-amount detecting section 25g may detect other change amounts like (E) to (K) below. The image-change-amount detecting section 25g may detect (E) a change in brightness of an endoscopic image (screen) in the endoscopic image, (F) a change in a shape of a branch, (G) a change in length of a spur, (H) a change in an angle of the spur, (I) a defect of a visual field, (J) an explanatory diagram of an operation for monitoring changes other than a change in a branch of a bronchus in the endoscopic image, and (K) a change in a blur of a feature section in the endoscopic image (E) to (K) are explained in order from the case of (E).

(E) Detect a Change in Brightness of an Endoscopic Image (Screen) in the Endoscopic Image In the case of (E), the brightness-change-amount detecting section 25i (of the image-change-amount detecting section 25g) acquires an endoscopic image at a time interval of a fixed time set in advance and continuously performs an operation for monitoring an area of a dark part in the acquired endoscopic image. Positions of the distal end of the insertion section 11 in the case of the acquisition of the endoscopic image are indicated by P1, P2, . . . , and P5 in FIG. 11.

Figure 11:
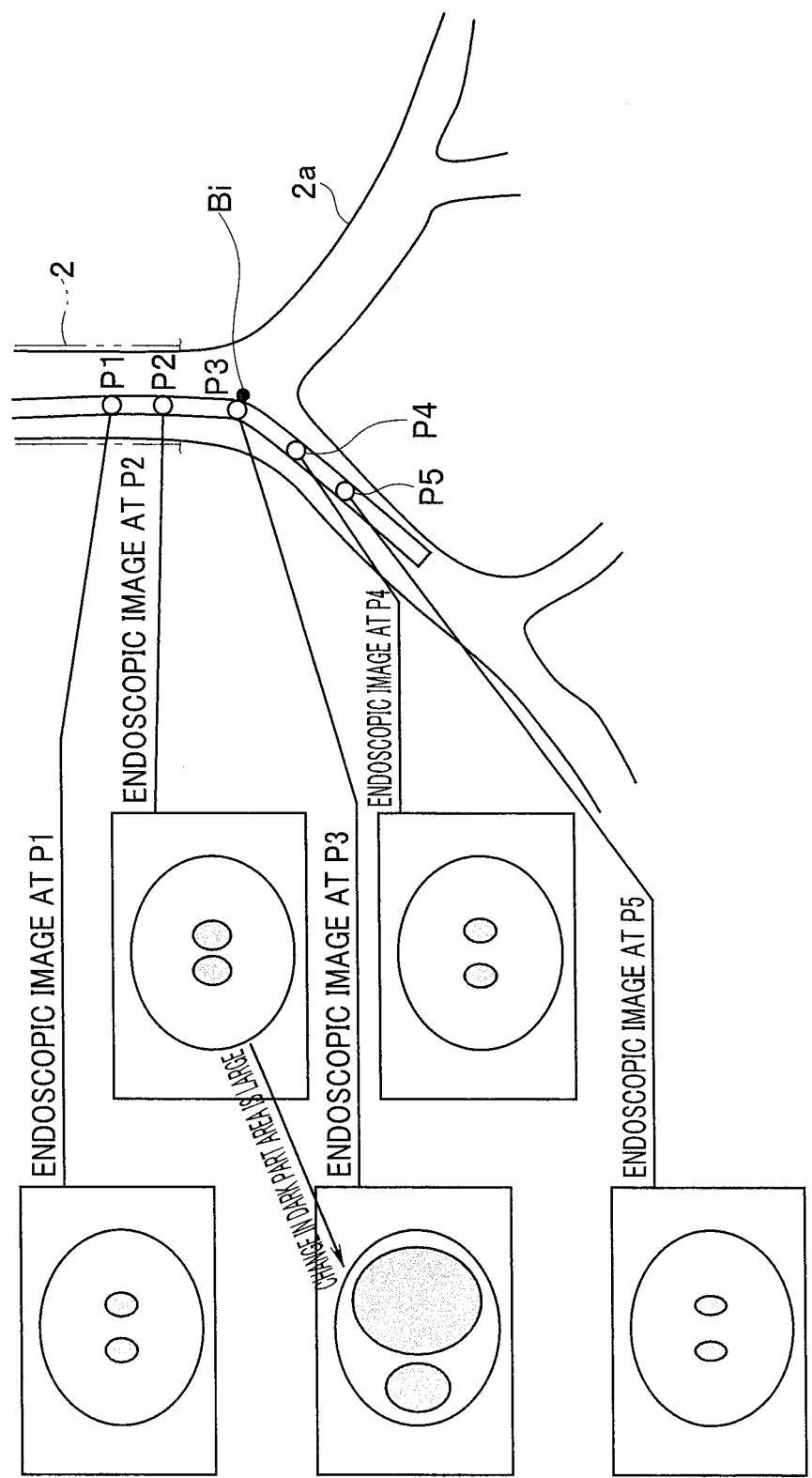
FIG. 11 is an explanatory diagram of a case in which a change in an area of a dark part in an endoscopic image is detected.

The area of the dark part indicates a total area of image portions where brightness is a specified value or less in the endoscopic image. In FIG. 11, a branch portion in a lumen portion on a distal end forward side of the insertion section 11 in the bronchus 2 is recognized as the dark part. For example, an area change of the dark part in the case in which the distal end of the insertion section 11 moves from the position P1 to the position P2 is small. However, in the position P3, since the distal end of the insertion section 11 approaches the branch region where the bronchus 2 branches, the area of the dark part greatly changes compared with the position P2. When detecting that the area of the dark part greatly changes by a set value or more, the brightness-change-amount detecting section 25i or the condition determining section 26b performs control to record (predetermined) information including a VBS image in the information recording section 27 in a position where the area of the dark part changes (P3 in the case of FIG. 11).

Note that, by detecting, on the basis of a change in the number of branch portions detected as dark parts (e.g., a change from two to one or one to two), the change as a large change amount of the area of the dark part, information including a VBS image may be recorded in the information recording section 27 when the change is detected.

A change amount of brightness is not limited to be detected from the change amount of the area of the dark part. An average of brightness of the endoscopic image may be calculated and, when the average is a change amount equal to or larger than a threshold, the information including the VBS image may be recorded in the information recording section 27.

Besides every fixed time or every fixed distance, the interval for acquiring the endoscopic image may be associated with timing for acquiring a distal end position of the insertion section 11. Note that when the information including the VBS image is recorded, the position where the information is recorded is not limited to the position where the brightness such as the area of the dark part changes by the set value or more and may be positions before and after the position.

When the information is recorded in the position of the position P3, the change amount that the surgeon can easily compare visually such as the area of the dark part is adopted as the change amount of the feature section in the image. Therefore, even when the information is displayed as the candidate information, the alignment can be easily performed visually.

(F) Detect a Change in a Shape of a Branch

Figure 12:
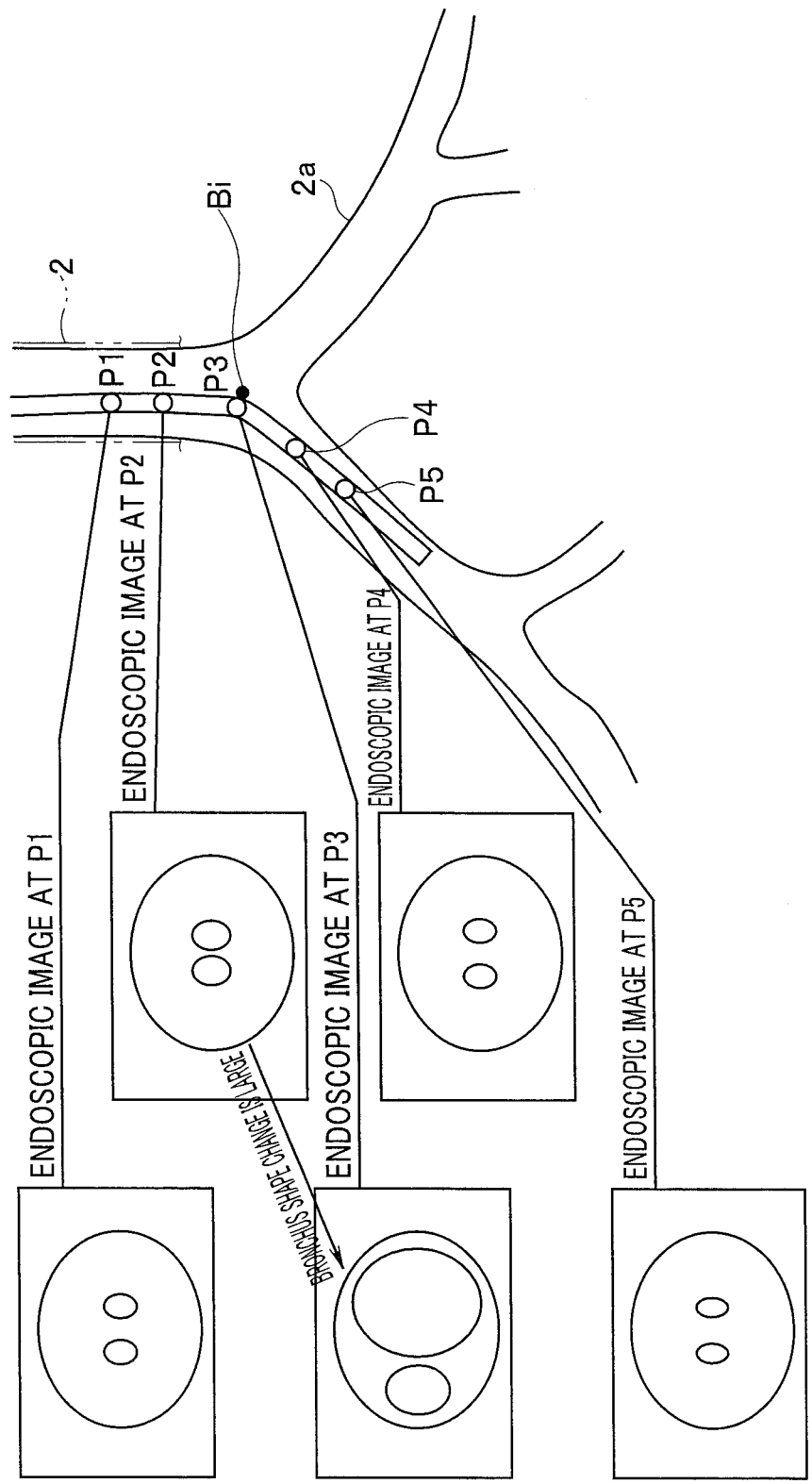
FIG. 12 is an explanatory diagram of a case in which a change in a shape of a branch in the endoscopic image is detected.

FIG. 12 shows a portion of a branch shape of the bronchus 2 in an extracted state. In this case, when the insertion section 11 is inserted into the bronchus 2 as shown in FIG. 12, the shape-change-amount detecting section 25j of the image-change-amount detecting section 25g detects a change amount of a shape of a feature section in an endoscopic image.

More specifically, as indicated by the positions P1, P2, . . . , and P5 in FIG. 12, the shape-change-amount detecting section 25j acquires an endoscopic image, for example, at a fixed interval or a fixed time interval and continuously performs an operation for monitoring, for example, a branch shape of the bronchus 2 in the acquired endoscopic image.

In FIG. 12, the branch shape of the bronchus 2 is shown in an extracted state together with endoscopic images acquired in the respective positions Pj (j=1, 2, . . . , and 5).

More specifically, a change in a bronchus branch shape in the case in which the distal end of the insertion section 11 moves from the position P1 to the position P2 is small. However, in the position P3, since the distal end of the insertion section 11 approaches the branch region where the bronchus 2 branches, the bronchus branch shape greatly changes compared with the position P2. When detecting that the bronchus branch shape greatly changes (more than a set value), the shape-change-amount detecting section 25j records information including a VBS image in the information recording section 27 in a position where the bronchus branch shape changes (P3 in FIG. 12).

Besides every fixed time or every fixed distance, an interval for acquiring the endoscopic image may be associated with the timing for acquiring the distal end position of the insertion section 11.

In the case of (F), a change amount that the surgeon can easily compare visually like the change in the bronchus branch shape is adopted as the change amount of the feature section in the image. Therefore, even when the change amount is displayed as the candidate information, the alignment can be easily performed visually.

(G) Detect a Change in Length of a Spur

In this case, when the insertion section 11 is inserted into the bronchus 2 as shown in FIG. 13(A), the spur-change-amount detecting section 25k of the image-change-amount detecting section 25g detects a change amount of length of a spur in an endoscopic image. In FIG. 13(A), the length of the spur is shown in an extracted state together with endoscopic images acquired in the respective positions Pj (j=1, 2, . . . , and 5). Note that the length of the spur is length of a boundary in a branch section where the lumen of the bronchus 2 branches into two.

As shown in FIG. 13(A), at the positions P1, P2, . . . , and P5 at the fixed interval or the fixed time interval, the spur-change-amount detecting section 25k (of the image-change-amount detecting section 25g) acquires endoscopic images and continuously performs an operation for monitoring, for example, the length of the spur of the bronchus 2 in the acquired endoscopic images.

Figure 13:
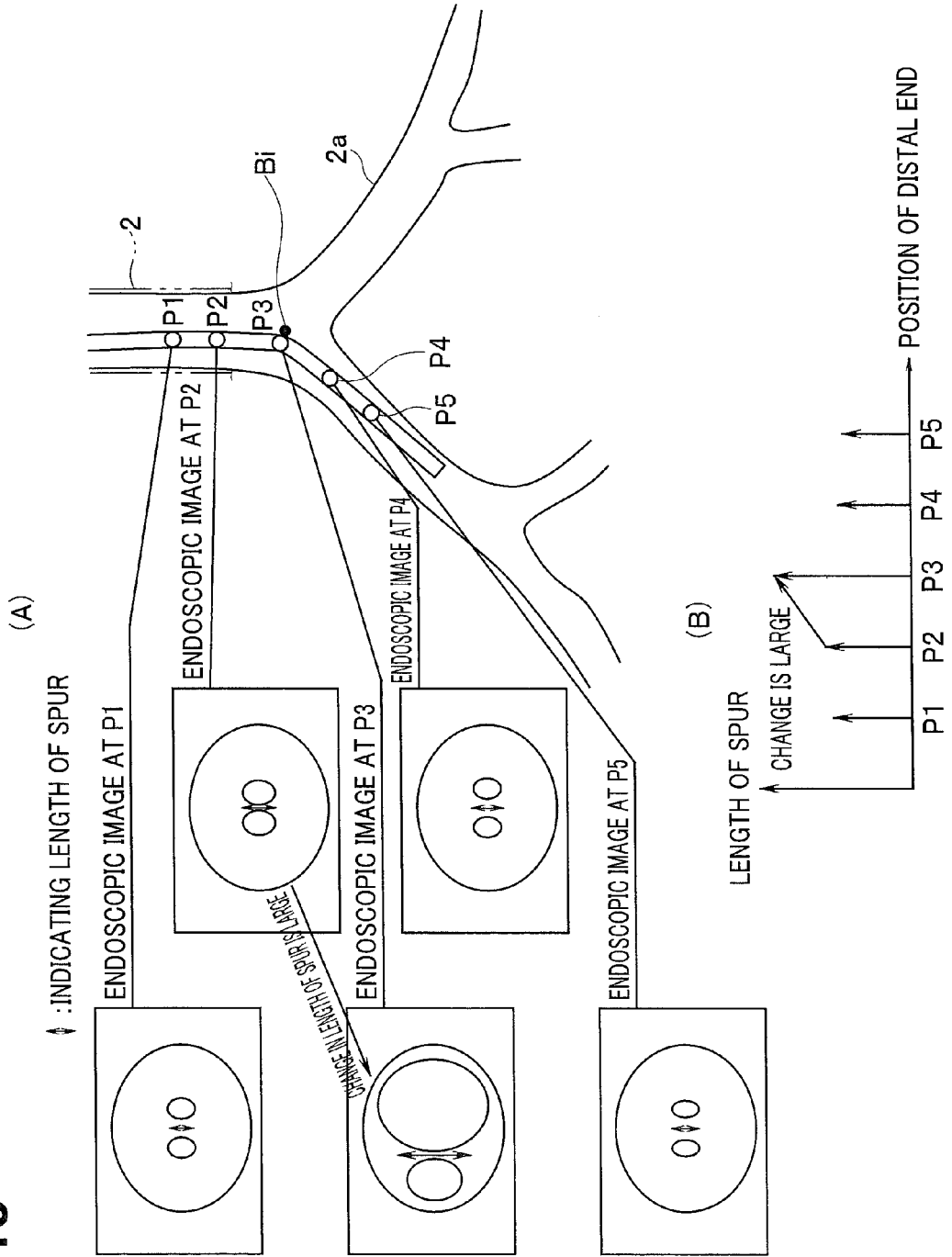
FIG. 13 is an explanatory diagram of a case in which a change in length of a spur in the endoscopic image is detected.

FIG. 13(B) shows a relation between the position Pj of the distal end of the insertion section 11 and the length of the spur. As it is seen from FIG. 13(A) and FIG. 13(B), for example, a change in the length of the spur in the case in which the distal end of the insertion section 11 moves from the position P1 to the position P2 is small. However, in the position P3, since the distal end of the insertion section 11 approaches the branch region where the bronchus 2 branches, the length of the spur greatly changes compared with the position P2. When detecting that the length of the spur greatly changes (more than a set value), the spur-change-amount detecting section 25k performs control to record information including a VBS image in the information recording section 27 in a position where the length of the spur changes (P3 in FIG. 13).

Besides every fixed time or every fixed distance, an interval for acquiring the endoscopic image may be associated with the timing for acquiring the distal end position of the insertion section 11.

In the case of (G), a change amount that the surgeon can easily compare visually like the change in the length of the spur is adopted as the change amount of the feature section in the image. Therefore, even when the change amount is displayed as the candidate information, the alignment can be easily performed visually.

(H) Detect a Change in an Angle of a Spur

In this case, when the insertion section 11 is inserted into the bronchus 2 as shown in FIG. 14(A), the spur-change-amount detecting section 25k of the image-change-amount detecting section 25g detects a change amount of an angle (a direction) of a spur in an endoscopic image. In FIG. 14(A), the angle of the spur is shown in an extracted state together with endoscopic images acquired in the respective positions Pj (j=1, 2, . . . , and 5). Note that the angle of the spur is a direction in a longitudinal direction of a boundary portion in the branch section where the lumen of the bronchus 2 branches into two or an angle formed with respect to a reference direction.

As indicated by the positions P1, P2, . . . , and P5 in FIG. 14(A), the spur-change-amount detecting section 25k (of the image-change-amount detecting section 25g) acquires an endoscopic image, for example, at a fixed interval or a fixed time interval and continuously performs an operation for monitoring, for example, the angle of the spur of the bronchus 2 in the acquired endoscopic image.

Figure 14:
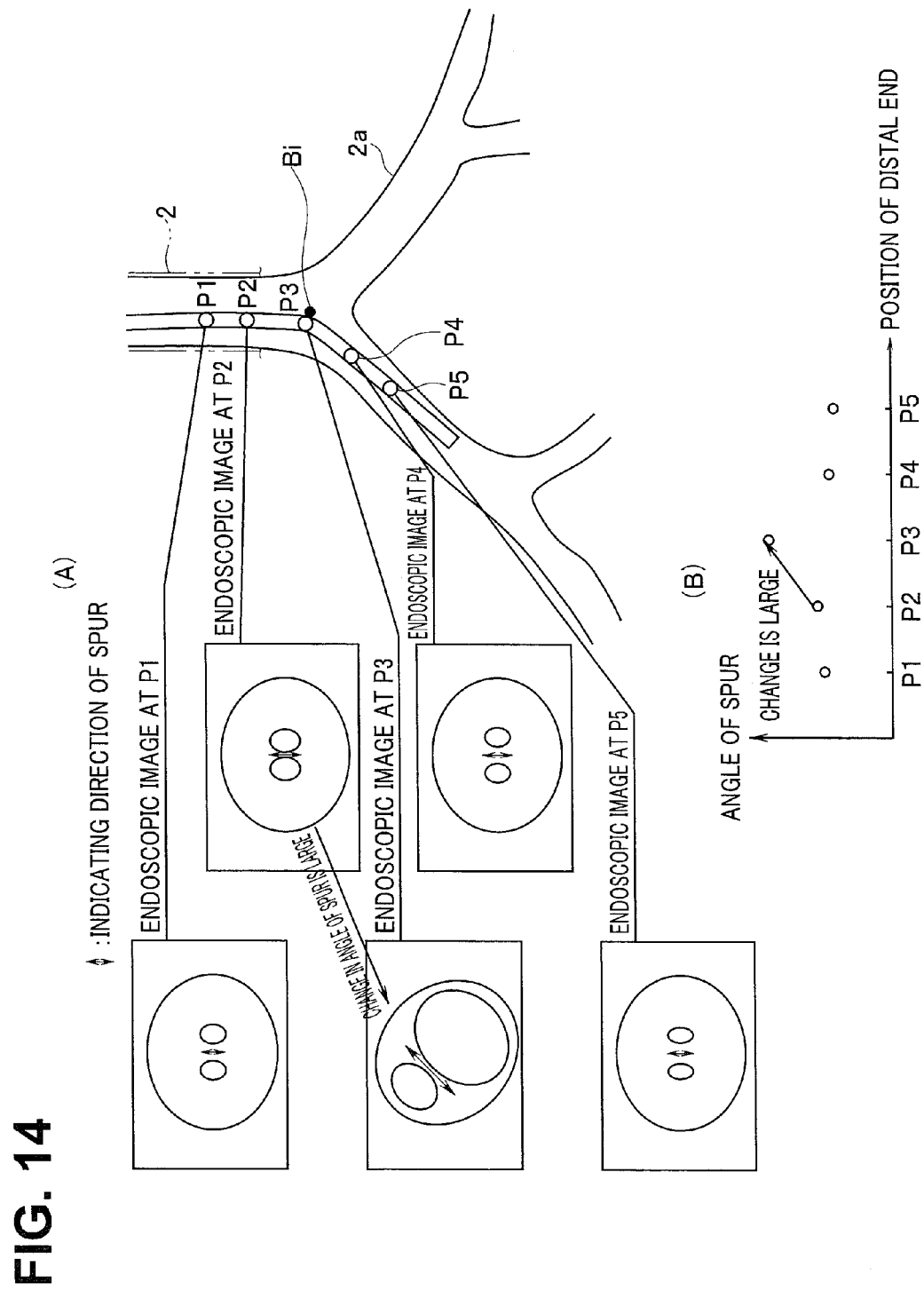
FIG. 14 is an explanatory diagram of a case in which a change in an angle of the spur in the endoscopic image is detected.

FIG. 14(B) shows a relation between the position Pj of the distal end of the insertion section 11 and the angle of the spur. As it is seen from FIG. 14(A) and FIG. 14(B), for example, a change in the angle of the spur in the case in which the distal end of the insertion section 11 moves from the position P1 to the position P2 is small. However, in the position P3, since the surgeon twists the insertion section 11 to bring the insertion section 11 close to the branch region where the bronchus 2 branches, the angle of the spur greatly changes compared with the position P2. When detecting that the angle of the spur greatly changes (more than a set value), the spur-change-amount detecting section 25k performs control to record information including a VBS image in the information recording section 27 in a position where the angle of the spur changes (P3 in FIG. 14).

Besides every fixed time or every fixed distance, an interval for acquiring the endoscopic image may be associated with the timing for acquiring the distal end position of the insertion section 11.

In the case of (H), a change amount that the surgeon can easily compare visually like the change in the angle of the spur is adopted as the change amount of the feature section in the image. Therefore, even when the change amount is displayed as the candidate information, the alignment can be easily performed visually.

(I) Detect a Defect of a Visual Field

Figure 15:
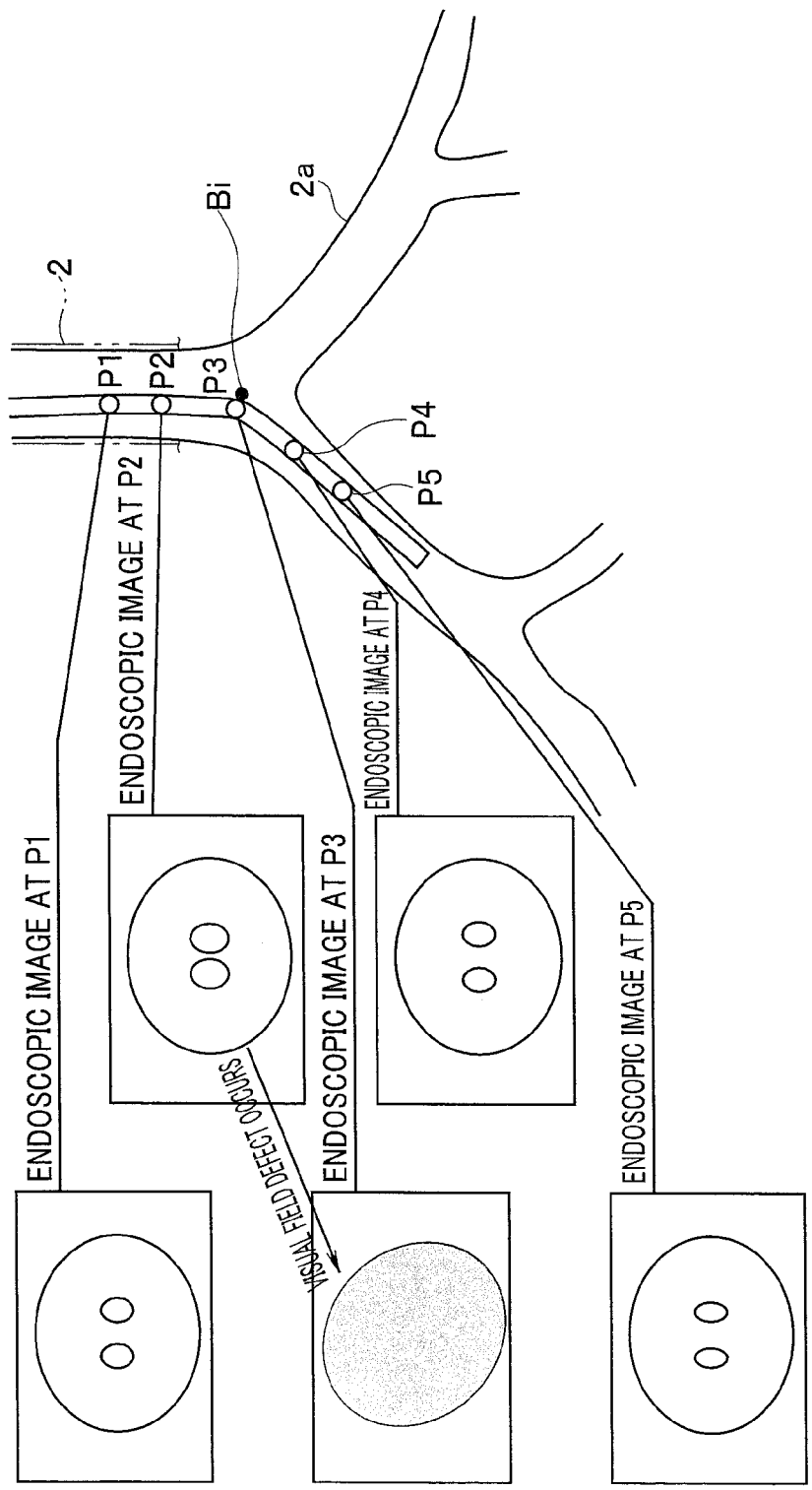
FIG. 15 is an explanatory diagram of a case in which a change to a defect of a visual field in the endoscopic image is detected.

In this case, when the insertion section 11 is inserted into the bronchus 2 as shown in FIG. 15, the visual-field-defect detecting section 25l of the image-change-amount detecting section 25g detects occurrence of a visual field defect in an endoscopic image.

The visual-field-defect detecting section 25l determines (the occurrence of) the visual field defect according to whether a branch on the distal end side of the lumen or a dark part is reflected to a distinguishable degree in an endoscopic image picked up in the bronchus. Assuming that a smudge covers an entire visual field, the visual-field-defect detecting section 25l determines that a visual field defect occurs when brightness of the endoscopic image is darker than predetermined brightness and a dark region extends to substantially the entire endoscopic image.

Therefore, for example, the brightness-change-amount detecting section 25i has the function of the visual-field-defect detecting section 25l.

In FIG. 15, an overview of endoscopic images acquired in the respective positions Pj (j=1, 2, . . . , and 5) is shown. As indicated by the positions P1, P2, . . . , and P5, the visual-field-defect detecting section 25l (of the image-change-amount detecting section 25g) acquires an endoscopic image, for example, at a fixed interval or a fixed time interval and continuously performs an operation for monitoring, for example, the visual field defect in the acquired endoscopic image. In an example shown in FIG. 15, when the distal end of the insertion section 11 moves from the position P2 to the position P3, the visual-field-defect detecting section 25l detects the occurrence of the visual field defect. In the position P2 immediately before the change, the visual-field-defect detecting section 25l records information including a VBS image in the information recording section 27.

Besides every fixed time or every fixed distance, an interval for acquiring the endoscopic image may be associated with the timing for acquiring the distal end position of the insertion section 11.

In the case of (I), a change amount that the surgeon can easily compare visually like the visual field defect is adopted as the change amount of the feature section in the image. Therefore, it is easy to grasp a state in which information is recorded.

Note that the shape-change-amount detecting section 25j explained above detects the change amount of the branch shape in the bronchus. However, the information may be recorded when the bronchus shape changes to a structure or a shape other than the branch shape, in other words, when the branch shape changes to a shape other than the branch shape.

Figure 16:
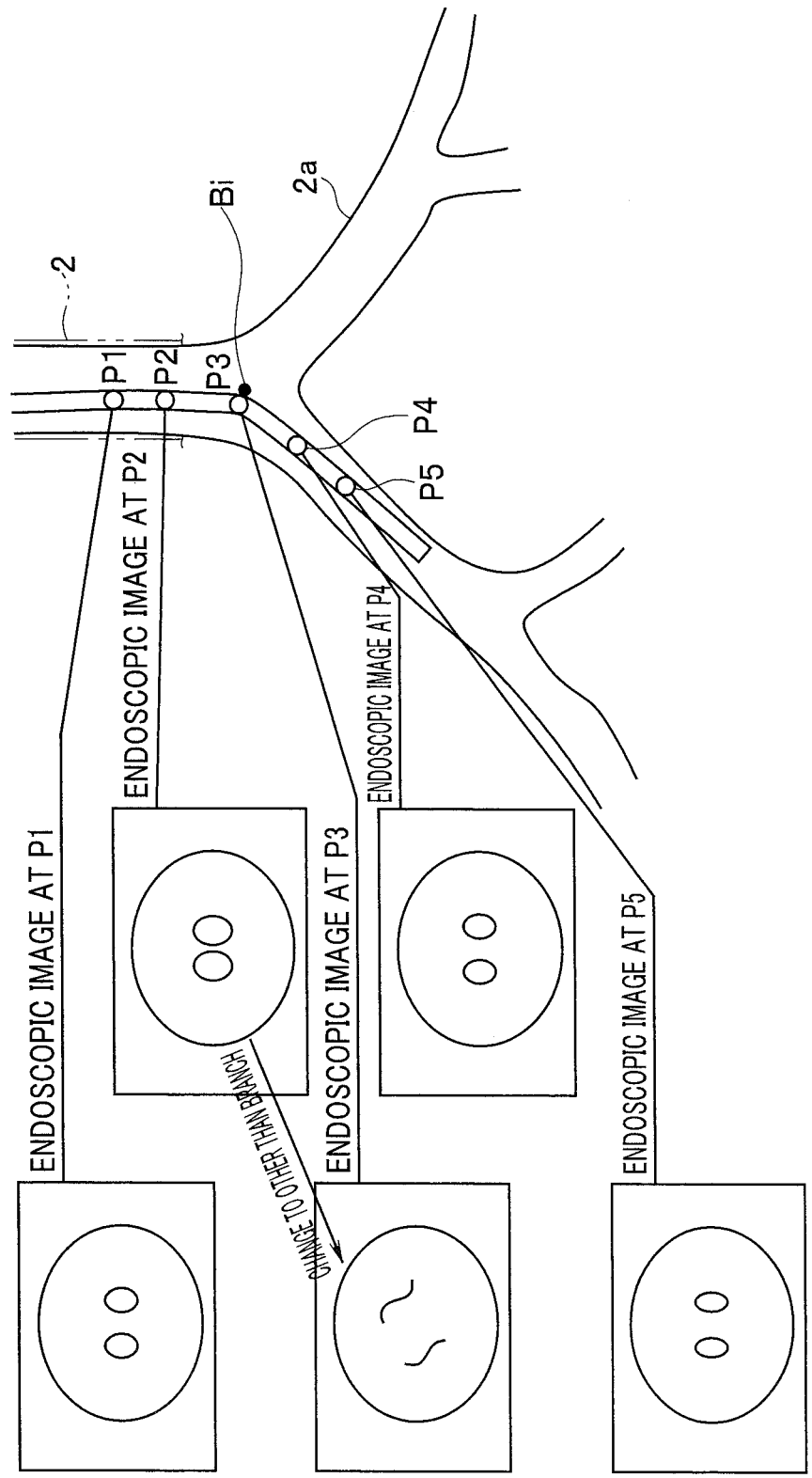
FIG. 16 is an explanatory diagram of a case in which a change to other than the branch of the bronchus in the endoscopic image is detected.

(J) Detect a Change Other than the Branch of the Bronchus in an Endoscopic Image In this case, when the insertion section 11 is inserted into the bronchus 2 as shown in FIG. 16, the shape-change-amount detecting section 25j of the change-amount detecting section 25g continuously performs an operation for monitoring whether the branch of the bronchus 2 in a picked-up endoscopic image of an inside of the bronchus 2 is present in the endoscopic image. When the bending section 19 of the insertion section 11 is bent or the insertion section 11 is twisted by the surgeon and the shape-change-amount detecting section 25j determines that the branch is absent in the endoscopic image, the shape-change-amount detecting section 25j records information including a VBS image in a position immediately before the branch in the information recording section 27.

As shown in FIG. 16, as indicated by the positions P1, P2, . . . , and P5, the shape-change-amount detecting section 25j (of the image-change-amount detecting section 25g) acquires an endoscopic image, for example, at a fixed interval or a fixed time interval, extracts, for example, a branch shape portion in the acquired endoscopic image, and continuously performs an operation for monitoring presence or absence of the branch. In FIG. 16, when the distal end of the insertion section 11 moves from the position P2 to the position P3, the shape-change-amount detecting section 25j determines that the endoscopic image changes to a state in which the branch is absent. In the position P2 immediately before the change, the shape-change-amount detecting section 25j performs control to record information including a VBS image in the information recording section 27.

Besides every fixed time or every fixed distance, an interval for acquiring the endoscopic image may be associated with the timing for acquiring the distal end position of the insertion section 11.

In the case of (J), a change amount that the surgeon can easily compare visually like the change in the presence or absence of the branch shape is adopted as the change amount of the feature section in the image. Therefore, it is easy to grasp a state in which information is recorded.

(K) Detect a Change in a Blur of a Feature Section in an Endoscopic Image

Figure 17:
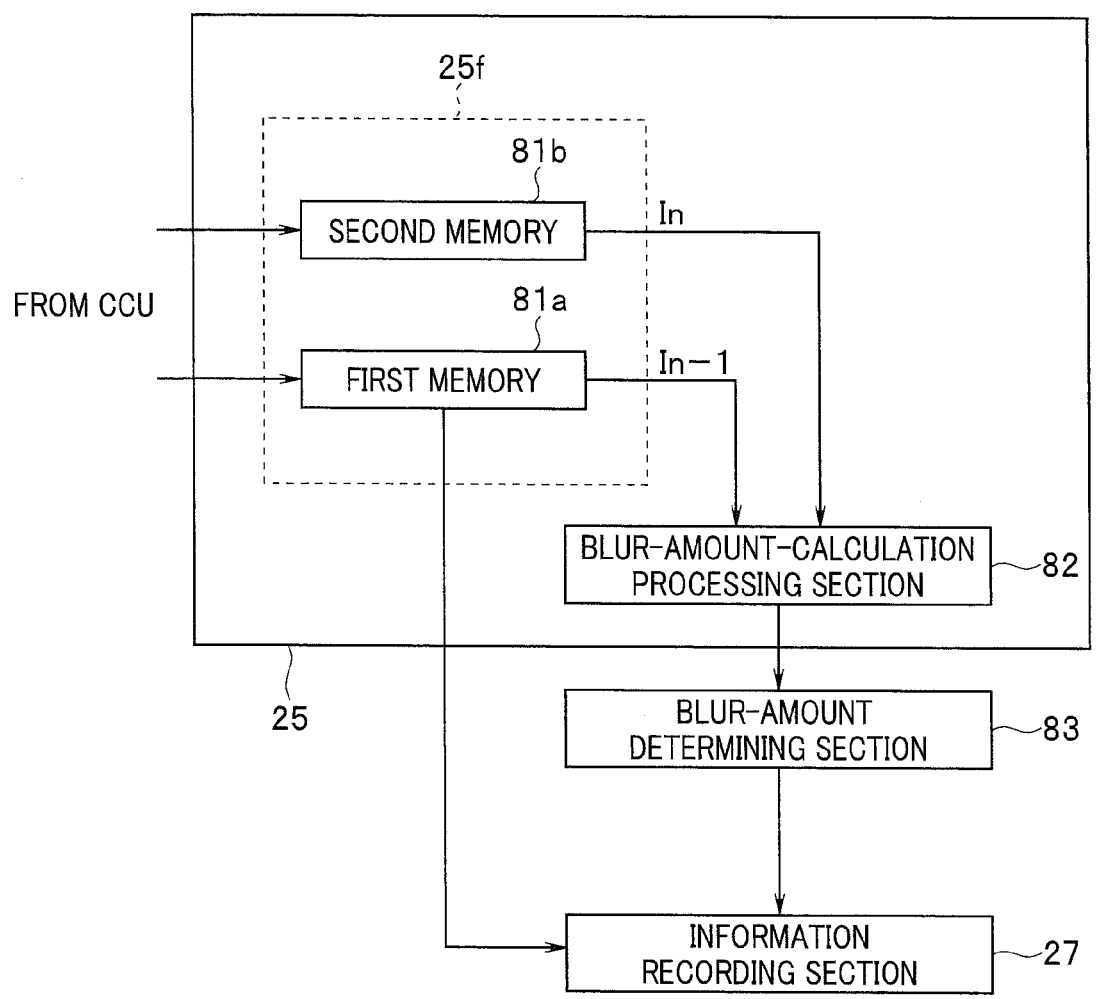
FIG. 17 is an explanatory diagram of a case in which a change in a blur of a feature section in the endoscopic image is detected.

In this case, as shown in FIG. 17, the image processing section 25 alternately stores, in a first memory 81a and a second memory 81b in the image memory 25f, image signals sequentially inputted at a predetermined time interval (e.g., 1/30 s or 1/60 s) from the CCU 8A. For example, a latest n-th image In is stored in the second memory 81b and an n−1-th image In−1 one frame or one field before the n-th image In is stored in the first memory 81a.

The n−1-th image In−1 and the n-th image In picked up in frames or fields adjacent to each other are inputted to a blur-amount-calculation processing section 82. The blur-amount-calculation processing section 82 performs calculation for calculating, as a motion vector amount representing a blur amount, a corresponding point in the other image with respect to a point set in one image (e.g., the image In).

The motion vector amount calculated by the blur-amount-calculation processing section 82 is inputted to a blur-amount determining section 83. The blur-amount determining section 83 regards the calculated motion vector amount as a blur amount, determines whether magnitude (an absolute value) of the motion vector amount exceeds a specified value, and records information including a VBS image as candidate information according to a determination result. Note that the condition determining section 26b shown in FIG. 1 may include a function of the blur-amount determining section 83.

The blur-amount-calculation processing section 82 sets, in a template, a range of W×H pixels centering on a center point of the image In and searches for a corresponding point on the image In−1 corresponding to the center point. The search for the corresponding point is performed by calculating, for example, an SAD (sum of absolute differences) of luminance. When a pixel value of the template is represented as t(x, y) and a pixel value of a search target image is represented as g(x, y), in general, F(u, v), which is the SAD in a coordinate (u, v), is calculated by the following Equation (4).

$$F(u,v)=\Sigma_i\Sigma_j|g(i+u,j+v)-t(i,j)| \quad (4)$$

Note that $\Sigma_i$ and $\Sigma_j$ respectively indicate that calculation for adding |g−t| at width W and height H of the template in which i is within $N_W$ and within $N_H$ is performed. When width of the template is represented as W and height of the template is represented as H, $-W/2 \leq N_W \leq W/2$ and $-H/2 \leq N_H \leq H/2$. A center coordinate of the image In−1 equivalent to the image In is represented as (Ox, Oy). F(u, v) is calculated in a range of $Ox-W/2 \leq u \leq Ox+W/2$ and $Oy-H/2 \leq v \leq Oy+H/2$. A coordinate (Ex, Ey) at time when F(u, v) is the smallest is the corresponding point.

A motion vector m is calculated by Equation (5) from the coordinate (Ex, Ey) of the corresponding point to the center coordinate (Ox, Oy) of the image In.

$$m=(Ex-Ox,Ey-Oy) \quad (5)$$

A calculation method for the motion vector m is as explained above.

When processing for calculating the motion vector m as a blur amount ends according to the calculation of the motion vector m, the blur-amount determining section 83 compares magnitude of the motion vector m with a specified value. When determining that the magnitude of the motion vector m is larger than the specified value, the blur-amount determining section 83 determines that a blur change exceeding a specified value occurs. The blur-amount determining section 83 outputs a recording instruction signal (or a storage instruction signal) for recording a VBS image to the information recording section 27.

The information recording section 27, which receives the recording instruction signal, records, as a candidate image, an image of the first memory 81a of the image memory 25f before the occurrence of the blur exceeding the specified value. This operation for recording the candidate image is performed every time the recording instruction signal is inputted. The candidate image is accumulated in the information recording section 27.

By repeating the operation explained above, when the blur of the endoscopic image is larger than the specified value, it is possible to accumulate, as the candidate image, an endoscopic image immediately before the endoscopic image. Note that, as a method of detecting a blur of the endoscopic image, calculation by SHIFT (scale-invariant feature transform) may be adopted. When feature points corresponding to respective images cannot be calculated or when a high-frequency component decreases by a specified value or more in a frequency analysis of an image, this may be recorded in the same manner. The same effect is obtained in such a case.

Note that, in the embodiments explained above, a representative combination is explained. However, information may be recorded by a combination other than the combination explained above.

That is, the present invention also includes a configuration and a method of any combination concerning the first condition and the second condition in the embodiments explained above.

The condition-information recording section 27a functioning as the condition-information recording means is explained as respectively recording the information of the plurality of candidate conditions and the candidate information that can be set as the first condition and the second condition. However, the condition-information recording section 27a may record, without using the information of the candidate conditions and the candidate information, a plurality of pieces of condition information (or information) that can be set as the first condition and the second condition. The condition-information recording section 27a may designate, without recording the plurality of pieces of condition information (or information), condition information desired by the surgeon or the like.

Note that, in the above explanation, when an instruction signal for performing the re-alignment is inputted to the control section 26 from the input apparatus 31 or the like, the information recorded in the information recording section 27 is displayed (presented) as the candidate information on the monitor 32 functioning as the display means.

The present invention is not limited to this case. For example, the information recorded in the information recording section 27 may be displayed (presented) as the candidate information on the monitor 32 functioning as the display means at predetermined timing.

For example, the user may perform, from the input apparatus 31 or the like, an input for setting a time interval or a condition for displaying the candidate information to the control section 26. When the time interval or the condition matches the set time interval or the condition, the control section 26 may perform control for reading out information from the information recording section 27 and display candidate information including a VBS image on the monitor 32 through the image processing section 25.

In a configuration including image comparing means for comparing image information picked up by image pickup means and a virtual endoscopic image and display means for displaying, at predetermined timing, a virtual endoscopic image recorded in information acquiring means, the information acquiring means may acquire at least position information of the image pickup means on the basis of a comparison result of the image comparing means.

Note that when a bronchus diameter detected by the bronchus-diameter-change-amount detecting section 25e is smaller than the reference bronchus diameter Dre and a change amount of a feature section such as a spur detected by the image-change-amount detecting means 25g changes by the set value or more, the information including the VBS image is recorded in the information recording section 27. However, when the change amount changes to be a maximum or a peak, the information-recording control section 26c or the like may record, in the information recording section 27, information including a position and a posture of the distal end of the insertion section 11, in which the change amount is the maximum or the peak, and a VBS image corresponding to the position and the posture.

The present invention is not limited to, for example, the configuration shown in FIG. 1 explained above or may be only a basic configuration (element) described in claim 1 or, in this basic configuration, a singularity or a plurality of components may be selectively added.

What is claimed is:

1. An endoscope system comprising:
   an endoscope including an image sensor configured to pick up an image of a lumen organ of a subject;
   a first memory configured to record three-dimensional image information of a lumen organ of the subject acquired from a medical diagnosis apparatus different from the endoscope; and
   a processor comprising hardware, wherein the processor is configured to:
     estimate a position of a distal end of the endoscope;
     acquire, on the basis of the three-dimensional image information recorded by the first memory, a lumen diameter of the lumen organ of the subject at the position of the distal end of the endoscope estimated;
     determine, on the basis of the lumen diameter acquired and a reference lumen diameter set in advance, whether the lumen diameter acquired is smaller than the reference lumen diameter;
     detect, when the processor determines that the lumen diameter acquired is smaller than the reference lumen diameter, a change amount of a predetermined parameter concerning an endoscopic image picked up by the image sensor involved in an inserting action of the endoscope, from the endoscope image; and
     generate, on the basis of the three-dimensional image information recorded by the first memory, a virtual endoscopic image endoscopically rendered from any visual point position,
   wherein the endoscope system further comprises:
     a second memory configured to record, when the change amount of the predetermined parameter concerning the endoscopic image detected is larger than a reference set value set in advance, the position of the distal end of the endoscope and the virtual endoscopic image corresponding to the position of the distal end of the endoscope.

2. The endoscope system according to claim 1,
   wherein the processor is further configured to:
     determine whether the change amount of the predetermined parameter detected changes by the reference set value set in advance or more, and
     when the processor determines that the change amount of the predetermined parameter changes by the reference set value set in advance or more, the second memory is configured to record the virtual endoscopic image corresponding to the position of the distal end of the endoscope.

3. The endoscope system according to claim 2,
   wherein, when it is determined that the change amount of the predetermined parameter changes by the reference set value set in advance or more, the second memory is configured to further record information concerning an axial direction of the distal end of the endoscope.

4. The endoscope system according to claim 1,
   wherein the processor is configured to acquire a lumen diameter of the lumen organ on a surface perpendicular to a longitudinal direction of the distal end of the endoscope.

5. The endoscope system according to claim 1,
wherein the processor is configured to acquire a lumen diameter of the lumen organ on a surface perpendicular to a core line, which is a center line of a lumen of the predetermined lumen organ.

6. The endoscope system according to claim 1,
wherein the predetermined parameter is a shape in a branch region where a lumen of the lumen organ branches, and
wherein the processor is configured to detect a change amount of the shape in the branch region where the lumen of the lumen organ branches in the endoscopic image.

7. The endoscope system according to claim 6,
wherein the processor is configured to detect whether length of a branch boundary where the lumen branches or a direction in a longitudinal direction of the branch boundary changes by a set value or more as the shape change amount in the branch region where the lumen of the lumen organ branches.

8. The endoscope system according to claim 1,
wherein the predetermined parameter is brightness information in a branch region where a lumen of the lumen organ branches, and
wherein the processor is configured to detect the change amount of the brightness information in the branch region where the lumen of the lumen organ branches.

9. The endoscope system according to claim 1,
wherein the processor is configured to:
compare the endoscopic image picked up by the image sensor and the virtual endoscopic image generated; and
estimate the position of the distal end of the endoscope on the basis of a comparison result of the endoscope image and the virtual endoscopic image.

10. The endoscope system according to claim 9,
wherein the processor is configured to:
generate a lumen shape image of the predetermined lumen organ; and
perform control to, when the processor fails in an estimation of the position of the distal end of the endoscope based on a comparison result of the endoscope image and the virtual endoscopic image or when an instruction signal for presenting at least one information of the position of the distal end of the endoscope and the virtual endoscopic image corresponding to the position of the distal end of the endoscope is generated, display the virtual endoscopic image recorded in the second memory in a corresponding position in the lumen shape image, and
wherein the processor is configured to acquire the position of the distal end of the endoscope by comparing the virtual endoscopic image read out from the second memory and a present endoscopic image picked up by the image sensor.

11. The endoscope system according to claim 1,
wherein, when the change amount detected by the processor continuously changes in a state of exceeding the reference set value, the second memory is configured to record the virtual endoscopic image when the change amount is a maximum.

12. The endoscope system according to claim 1, further comprising:
a third memory configured to record a plurality of pieces of condition information as each of the reference set values set in advance concerning the reference lumen diameter and the predetermined parameter; and
an input device configured to selectively designate, from the third memory, condition information respectively used as the reference set values set in advance concerning the reference lumen diameter and the predetermined parameter.

13. The endoscope system according to claim 1,
wherein the processor is configured to estimate a posture of the distal end of the endoscope in addition to the position of the distal end of the endoscope, and
wherein when the change amount of the predetermined parameter concerning the endoscopic image detected is larger than the reference set value set in advance, the second memory is configured to record the position and the posture of the distal end of the endoscope.

* * * * *